(12) United States Patent
Cussac et al.

(10) Patent No.: US 11,311,194 B2
(45) Date of Patent: Apr. 26, 2022

(54) PHYSIOLOGICAL SENSOR FOR A NEAR-INFRARED SPECTROSCOPY AT DIFFERENT DEPTHS

(71) Applicant: BRAINDEX s.a.s, Marseilles (FR)

(72) Inventors: Thierry Cussac, Muret (FR); Antonio Luna Arriaga, Toulouse (FR)

(73) Assignee: BRAINDEX s.a.s, Marseilles (FR)

( * ) Notice: Subject to any disclaimer, the term of this patent is extended or adjusted under 35 U.S.C. 154(b) by 371 days.

(21) Appl. No.: 16/507,545

(22) Filed: Jul. 10, 2019

(65) Prior Publication Data

US 2019/0343395 A1 Nov. 14, 2019

Related U.S. Application Data

(63) Continuation of application No. PCT/FR2018/050046, filed on Jan. 9, 2018.

(30) Foreign Application Priority Data

Jan. 10, 2017 (FR) ...................................... 17/50207
May 3, 2017 (FR) ...................................... 17/53888

(51) Int. Cl.
 *A61B 5/00* (2006.01)
 *A61B 5/024* (2006.01)
 *A61B 5/026* (2006.01)

(52) U.S. Cl.
 CPC .......... *A61B 5/0075* (2013.01); *A61B 5/0261* (2013.01); *A61B 5/02433* (2013.01); *A61B 2562/046* (2013.01)

(58) Field of Classification Search
 CPC ............ A61B 5/0042; A61B 2562/046; A61B 5/0075
 See application file for complete search history.

(56) References Cited

U.S. PATENT DOCUMENTS

2012/0029345 A1* 2/2012 Mahfouz .................. A61B 5/24
 600/427
2013/0090541 A1 4/2013 MacFarlane et al.
(Continued)

FOREIGN PATENT DOCUMENTS

EP 1374778 1/2004
EP 2092880 8/2009
(Continued)

OTHER PUBLICATIONS

International Search Report for International Application PCT/FR2018/050046, dated Jul. 9, 2018.

*Primary Examiner* — Fabricio R Murillo Garcia
(74) *Attorney, Agent, or Firm* — Burris Law, PLLC

(57) ABSTRACT

A physiological sensor for near-infrared spectroscopy at various depths includes elementary modules, each provided with at least one element chosen among transmitters of near infrared beams and receivers that are photosensitive in near-infrared, wherein each elementary module is connected to an adjacent elementary module by means of an articulation coupled to an angle sensor configured to measure the angle of inclination between the two elementary modules, wherein the elementary modules are assembled in order to form an optoelectronic layer that can be configured between a planar configuration in a main plane in which each articulation has an angle of inclination that is zero with respect to the main plane, and a plurality of curved configurations in which at least one of the articulations has an angle of inclination that is not zero with respect to the main plane.

31 Claims, 9 Drawing Sheets

(56) References Cited

U.S. PATENT DOCUMENTS

| | | | | |
|---|---|---|---|---|
| 2013/0150726 A1* | 6/2013 | Riley | ................ | A61B 5/02042 |
| | | | | 600/473 |
| 2014/0275891 A1* | 9/2014 | Muehlemann | ....... | A61B 5/0275 |
| | | | | 600/328 |
| 2014/0371566 A1* | 12/2014 | Raymond | ............ | A61N 1/0492 |
| | | | | 600/386 |
| 2016/0022223 A1* | 1/2016 | Grundfest | .......... | A61B 5/14546 |
| | | | | 600/324 |

FOREIGN PATENT DOCUMENTS

| | | |
|---|---|---|
| EP | 2434942 | 4/2012 |
| WO | 2015070162 | 5/2015 |
| WO | 2015109005 | 7/2015 |

\* cited by examiner

PHYSIOLOGICAL SENSOR FOR A NEAR-INFRARED SPECTROSCOPY AT DIFFERENT DEPTHS

CROSS-REFERENCE TO RELATED APPLICATIONS

This application is a continuation of International Application No. PCT/FR2018/050046, filed on Jan. 9, 2018, which claims priority to and the benefit of FR 17/50207 filed on Jan. 10, 2017 and FR 17/53888, filed on May 3, 2017. The disclosures of the above applications are incorporated herein by reference.

FIELD

The present disclosure relates to a physiological sensor for a near-infrared spectroscopy, as well as to a near-infrared spectroscopy system comprising such a physiological sensor.

BACKGROUND

The statements in this section merely provide background information related to the present disclosure and may not constitute prior art.

In vivo monitoring and/or imagery applications for use in the field of near-infrared spectroscopy for medical diagnosis applications and/or for physiological parameters monitoring include:

vascular volumes or blood volumes, and in particular subcutaneous vascular or blood volumes, such as a cortical or tissue blood volume or others;

volumes and concentrations of hemoglobins, and in particular oxyhemoglobin (HbO2) and deoxyhemoglobin (Hb);

reperfusion tests;

hemodynamic parameters such as tissue oxygen saturation (StO2), regional cerebral oxygen saturation (RScO2), cerebral autoregulation plateau;

volumes and concentrations of metabolites.

Near-infrared spectroscopy is a conventional technology in the medical field, which essentially consists in implementing, on the one hand, at least one emitter emitting a light beam in the near-infrared, with a length comprised between 650 and 1000 nanometers, which passes through the organic tissues (unlike visible light and ultraviolet) and, on the other hand, at least one photosensitive receiver which measures the absorption and scattering of the photons that have passed through the organic tissues.

In this specific spectrum of the near-infrared, it is possible to detect the electronic transitions of chromophores that are oxyhemoglobin and deoxyhemoglobin. Indeed, these molecules present in the blood have their absorption spectrum change in the near-infrared depending on their interaction with oxygen, because they absorb the near-infrared spectrum in a differential manner according to their concentration and their interaction with oxygen.

The wavelengths used by the emitter are selected in order to be sensitive to these biological molecules (generally between 650 and 1000 nanometers), the oxyhemoglobin absorbing more the wavelengths between 800 and 1000 nanometers while the deoxyhemoglobin absorbs more the wavelengths between 650 and 800 nanometers. The absorption of near-infrared light waves by oxyhemoglobin and deoxyhemoglobin is used in particular as a basis for calculating the oxygen saturation in application of the Beer-Lambert law, which stipulates that the concentration of a substance can be measured according to its light absorption degree.

The beam of photons emitted by an emitter and received by a receiver takes the shape of a diffuse light arc which passes through the organic tissues, wherein the penetration depth of the beam between the emitter and the receiver corresponds to about one third of the distance between the emitter and the receiver.

Thus, the distance between the emitter and the receiver has a considerable impact on the penetration depth of the beam into the organic tissues. The more distant is a receiver from the emitter, the more the beam collect thereby would have crossed a large distance (or depth) in the organic tissues, thus probing deeper layers. A distance between the emitter and the receiver that is large enough is therefore necessary to provide sufficient penetration that allows providing a measurement on deep layers and not on surface layers. However, increasing this emitter—receiver distance will lead to an increased diffusion/absorption of the emitted signal having the consequence of decreasing the spatial resolution of the measurement and attenuating the received signal. Indeed, the spatial resolution of near-infrared spectroscopy does not exceed 0.5 millimeters immediately beneath the skin, and degrades as the depth increases.

A known medical application of infrared spectroscopy is the measurement of cerebral activity or cerebral oximetry, by following the curves of oxyhemoglobin and deoxyhemoglobin concentrations at a given intracranial depth.

For this application, it is known, in particular from documents WO 2015/109005 and EP 2 434 942, to use a physiological sensor comprising a flexible strip on which are mounted a near-infrared beam emitter and at least two near-infrared photosensitive receivers, including a proximal receiver separated from the emitter by a proximal distance and a distal receiver separated from the emitter by a distal distance which is larger than the proximal distance. Thus, the signal acquired by the proximal receiver comes from a more superficial (less deep) source and the signal acquired by the distal receiver includes this superficial area but also a deeper component. By subtracting the proximal signal from the distal signal, it is possible to obtain a value of a distal signal free of surface components.

Thus, it is provided to implement several emitters and/or several receivers, and to proceed with a spatial subtraction of signals acquired in the near-infrared spectroscopy at different depths in order to increase the selectivity in some medical applications, including the measurement of cerebral activity or cerebral oximetry. However, such physiological sensors known from documents WO 2015/109005 and EP 2 434 942 still have a limited selectivity.

This technique, consisting in implementing a spatial subtraction of signals acquired in the near-infrared spectroscopy at different depths, is also implemented for other applications, such as the monitoring of hemodynamic parameters or the imagery of vascular or blood volumes, as described in documents US 2016/0022223, US 2013/0150726 and WO 2015/070162.

The document US 2016/0022223 for a hemodynamic parameters monitoring application and the document US 2013/0150726 for an application for detecting a subcranial hematoma type blood volume, each proposes placing emitters and receivers on a flexible support strip for adapting the support strip to the portions of the body of a patient, such as the skull or a limb. However, the flexibility of the support strip brings an uncontrolled uncertainty on the relative positions between emitters and receivers, thus impairing the accuracy during spatial the subtraction operations and therefore, ultimately, a great inaccuracy in the results.

The document WO 2015/070162, in an application for imaging a subcutaneous blood volume, proposes in turn a physiological sensor comprising emitters and receivers mounted on a rigid support tray, whether flat or curved. However, the rigidity of the support tray contributes in limiting the resolution. For example, in the case of a flat support, all emitters and receivers are in the same plane, so that some of them will not be pressed against the concerned portion of the body of the patient, in particular if this portion is curved like a limb or a skull. Thus, such a sensor is functionally limited in its applications by its own dimensions as to the explorable tissue depth, as to its resolution and as to the cutaneous or tissue surface on which it is applied. This sensor is, for example, unsuitable for monitoring cerebral activity or cerebral oximetry over frontal hemispheres of a large panel of patients with variable cranial morphologies, since this sensor cannot be functionally applied over the roundness of the frontal hemispheres surface. Indeed, an air interface layer would appear between the cutaneous surface and the sensor, which would represent a source of diffusion parasitizing the near-infrared beams, thus raising a problem of graphical modeling of the signal and the accuracy of the measurements.

The state of the art can also be illustrated by the teaching of document US 2014/0275891 which discloses a physiological sensor for a near-infrared spectroscopy at different depths, which comprises three modules each provided with a support (segments) on which at least one optoelectronic component is disposed, wherein each support of a module is connected to the support of at least one adjacent module by means of an articulation hinge.

SUMMARY

The present disclosure proposes solving the aforementioned drawbacks by proposing a solution to be able to perform a near-infrared spectroscopy at different depths with increased resolution and reliability in the measurements.

The present disclosure provides a physiological sensor which allows performing three-dimensional imagery with an improved spatial resolution, and this for all portions of the body and in particular the curved parts such as an internal organ (e.g., heart, liver), a limb (e.g., arm, leg) or a skull.

The present disclosure provides a physiological sensor which is portable and can be easily manipulated by medical personnel.

to the present disclosure enables a near-infrared spectroscopy at different depths, which compensates for the variation of the optical paths in the traversed tissues due to the variation of the roundness of the examined surfaces, and this by means of the same physiological sensor, in particular in order to perform a three-dimensional imagery with an improved spatial resolution.

To this end, it proposes a physiological sensor for near-infrared spectroscopy at different depths, said physiological sensor integrating optoelectronic components comprising emitters of near-infrared beams and near-infrared photosensitive receivers, said physiological sensor comprising elementary modules each provided with at least one optoelectronic component, wherein each elementary module is connected to at least one adjacent elementary module by means of an articulation configured for a relative movement between the elementary modules according to several angles of inclination, wherein the elementary modules are assembled at least by means of the articulations and form an optoelectronic spread configurable between:

a planar configuration according to a main plane in which each articulation has a zero angle of inclination, and a set of curved conformations in which at least one of the articulations has a non-zero angle of inclination.

and wherein each articulation between two elementary modules is coupled to an angle sensor configured for a measurement of the angle of inclination between the two elementary modules.

Thus, because of the articulations with known angulations (thanks to the angle sensors) between the elementary modules, the elementary modules—and therefore the emitters and the receivers—can be positioned on the concerned portion of the body of the patient to be analyzed (for example a limb or an internal organ in an aseptic environment) in an accurate, known and controlled manner, thus contributing in adapting the shape of the physiological sensor the closest to the concerned portion of the body of the patient, while having an accurate control of the relative positionings and spacings between the emitters and the receivers; such a knowledge of these positionings and spacings can then be injected into an accurate and reliable calculation of spatial subtraction of signals acquired at different depths. This calculation can also take into account the angle of inclination of each articulation to compensate for the distribution of light in the biological tissues.

Such a physiological sensor thus forms an optoelectronic spread or a spread of optoelectronic components (namely the emitters and the receivers) that can conform to the cutaneous surface of any portion of the body of the patient, thanks to the articulations, as well as to the morphology of the underlying organ, or the organ of the patient, and enables an implementation of a near-infrared spectroscopy for in vivo detection of hemoglobins, circulating by nature only in the vascular network.

The articulations between the elementary modules enable continuous or almost-continuous contact of the optoelectronic components with the examination surface, without creating an intermediate air layer which would be a source of light diffusion.

Moreover, the angle of inclination of each articulation (or angle of inclination between two elementary modules) is known directly and in real-time thanks to the angle sensors, enabling an accurate and effective treatment to establish the spatial coordinates of the emitters and receivers of the different elementary modules.

Such a physiological sensor thus provides an answer to the problem of the normalization of the processed signals, and of the necessary compensation of the variation of the optical paths, induced by the variation of roundness from one examination surface to another, for the purpose of a three-dimensional pictorial representation, in particular by using the angle sensors that will actually contribute to achieving enhanced and reliable spatial resolution.

In a first variation, at least one articulation between two elementary modules is a flexible articulation comprising a flexible strip configured for a relative movement between the elementary modules by bending of the flexible strip.

Thus, the relative movement between two elementary modules at several angles of inclination is obtained by a bending (in the manner of folding/unfolding) of the flexible strip forming the flexible articulation connecting the two elementary modules. The optoelectronic spread, composed of the assembly of the elementary modules and articulations, therefore forms a spread at least partially flexible or flexible and adjustable to the morphology of the surface to be analyzed thanks to the bendings of the various flexible strips.

An articulation with a flexible strip is thus called flexible or flexible articulation, in the sense that it is adjustable in a continuous or non-discrete manner by bending of the flexible strip, thus providing a multiplicity of angles of inclination.

According to one possibility, each articulation between two elementary modules is a flexible articulation comprising a flexible strip configured for a relative movement between the elementary modules by bending of the flexible strip. In other words, all articulations are flexible articulations that bend to adapt to the morphology of the surface to be analyzed.

According to one feature, each elementary module comprises a rigid or flexible support on which at least one optoelectronic component is disposed, and the flexible strip of the flexible articulation between two elementary modules is connected between the supports of said two elementary modules.

In a form of this first variation, the physiological sensor comprises a flexible membrane on which the optoelectronic components are disposed and distributed into islets delimiting the elementary modules, and wherein the flexible strip of the flexible articulation between two elementary modules is formed by a portion of the flexible membrane extending between the islets delimiting said two elementary modules.

According to another feature, the flexible membrane comprises at least one elastomeric polymer layer in which the optoelectronic components are embedded at least partially.

According to another feature, for a flexible articulation comprising a flexible strip, this flexible articulation is coupled to an angle sensor comprising a flexible resistive sensor outputting an angle datum reflecting a variation of resistance as a function of the bending of the flexible strip.

In other words, the flexible articulation is coupled to a flexible resistive sensor or bending sensor. For this purpose, a technology allowing measuring angles accurately is used, based on the exploitation of variations of resistance occurring when a conductive material is curved; the flexible resistive sensor behaving as a passive potentiometer whose resistance varies as a function of the bending.

According to a first possibility, the flexible resistive sensor is integrated into the flexible strip, in other words the flexible strip which forms the flexible articulation between two elementary modules integrates (internally or at the surface) such a flexible resistive sensor, by using a conductive material at least partially embedded in the flexible strip or fastened at the surface on the flexible strip.

Alternatively, the flexible resistive sensor is offset with respect to the flexible strip, that is to say that the flexible resistive sensor is not located on the flexible strip but is shifted with respect to this flexible strip on an offset portion which will bend at the same time as or with the flexible strip. Thus, the flexible resistive sensor will be adapted to indirectly measure the bending of the flexible strip by directly measuring the bending of this offset portion.

With this first possibility, the flexible resistive sensors may thus be integrated into the above-described flexible membrane, in particular by being offset on the sides of the flexible membrane.

According to a second possibility, the flexible resistive sensor is integrated to a flexible blade fastened to the flexible strip, in particular in a detachable manner, so that a bending of the flexible strip results in a bending of the flexible blade.

In other words, the flexible resistive sensor comprises a conductive material at least partially embedded in the flexible blade or fastened at the surface on the flexible blade, and this flexible blade is attached on the flexible strip forming the flexible articulation between two elementary modules. The flexible blade being attached to the flexible strip, the latter bends with the flexible strip so that the measurement performed by the flexible resistive sensor integrated into the flexible blade reflects the bending of the flexible strip and therefore outputs a measurement of the angle of inclination between the two elementary modules.

Thus, the angle sensor function is provided on the flexible blade whereas the articulation function is provided by the flexible strip, thus dissociating the optoelectronic portion (the optoelectronic components connected by the flexible articulations) from the angle measuring portion (the angle sensors on the flexible blades).

In another variation, the physiological sensor comprises a flexible film on which flexible resistive sensors are disposed, wherein this flexible film is superimposed and fastened on the flexible membrane, and wherein this flexible film defines flexible blades superimposed or offset with respect to the flexible strips of the flexible articulations between the elementary modules, said flexible resistive sensors being provided on these flexible blades.

In other words, the flexible resistive sensors are provided on the flexible film which is in turn attached on the flexible membrane receiving the optoelectronic components, thus separating the optoelectronic portion (the flexible membrane) from the angle measuring portion (the flexible film).

According to another feature, the flexible film comprises at least one elastomeric polymer layer in which the flexible resistive sensors are at least partially embedded.

In a second variation, at least one articulation between two elementary modules is a semi-rigid articulation configured for a relative movement between the elementary modules according to several predefined discrete angles of inclination, wherein said semi-rigid articulation is configured to keep a stable inclination between two elementary modules in each of said angles of inclination, and to tilt between two distinct angles of inclination under the effect of a force applied on at least one of the two concerned elementary modules.

Such an articulation is semi-rigid, in the sense that, unlike the previously described flexible strip, this semi-rigid articulation is not adjustable in a continuous and non-stable manner, but rather in a discrete manner with several predefined angles of inclination wherein, for each angle of inclination, the articulation keeps this angle of inclination in a stable manner.

According to one possibility, a semi-rigid articulation is provided with notches for setting the angle of inclination between the two elementary modules according to several predefined values.

In another variation, a semi-rigid articulation is coupled to an angle sensor comprising electrical contactors, wherein each electrical contactor is coupled to a setting notch.

In other words, each setting notch is coupled to a contactor, all these contactors forming the angle sensor capable of establishing the measurement of the angle of inclination, each setting notch being indeed associated with an angle of inclination.

According to another possibility, a semi-rigid articulation is coupled to an angle sensor made in the form of a flexible resistive sensor attached on the articulation and comprising a flexible blade which bends with the articulation, said flexible resistive sensor outputting a measurement data reflecting a variation of resistance as a function of the bending of the flexible blade.

According to another possibility, each articulation (whether it is a flexible articulation or a semi-rigid articulation) is adjustable between −30 and +30 degrees for the angle of inclination between the two elementary modules.

According to another possibility, each semi-rigid articulation is adjustable according to several predefined angles of inclination separated in pairs by a constant angular step, in particular an angular step comprised between 5 and 15 degrees.

As non-limiting examples, each semi-rigid articulation may have the following angles of inclination, in degrees, [0, 5, 10, 15, 20, 25, 30] or [0, 10, 20, 30] or [0, 15, 30].

In another variation, each semi-rigid articulation comprises several balls cooperating with an elastic thrust element, said balls being movable within a curved rail with a predefined curvature and sliding inside a guide with the same curvature, and further comprises a cursor on the guide adapted to crush the balls according to the sliding of the rail within the guide, wherein the supports linked by the articulation are fastened respectively to one end of the rail and to one end of the guide.

Thus, such a semi-rigid articulation comprises a rail sliding within a guide, with the balls and the elastic thrust element on the rail. The rail and the guide abutting one inside the other represent an angle sector substantially corresponding to half the possible sector of the angle of inclination.

In this variation, the cursor of the guide can establish electrical contact with the crushed ball corresponding to the sliding of the rail within the guide, thus allowing establishing the angle of inclination.

Alternatively, each semi-rigid articulation comprises two full hinge half-faces, of about half the desired maximum sector of the angle of inclination, and having complementary reliefs that fit when said hinge half-faces are pressed against each other. These hinge half-faces are adapted to slide against each other in a controlled manner by applying a suitable force, so that these hinge half-faces slightly deviate to move from a setting notch to the next setting notch. A contactor can allow determining the position of the setting notch.

According to one feature, each elementary module comprises at least one optoelectronic component selected from the emitters and the receivers and disposed according to at least one of the following arrangements:
  at least one emitter and at least one receiver;
  at least two emitters of signals in distinct lengths in the near-infrared;
  at least one emitter disposed at the center of the elementary module and at least one receiver disposed at the periphery of the elementary module;
  at least one emitter disposed at the center of the elementary module and several receivers disposed at the periphery around said emitter;
  one or several emitter(s) and no receiver;
  one or several receiver(s) and no emitter.

According to another feature, in the planar configuration of the optoelectronic spread, the elementary modules are distributed into several rows and into several columns orthogonal to the rows.

Such a distribution into rows and columns is advantageous for the treatment according to a spatial subtraction method.

In another variation, each elementary module comprises a rigid or flexible support, on which at least one optoelectronic component is disposed, and each support comprises two opposite and parallel longitudinal edges, and two opposite and parallel transverse edges, and each articulation links two transverse edges contiguous to two adjacent respective supports, namely two longitudinal edges contiguous to two adjacent respective supports.

According to one feature, in the planar configuration of the optoelectronic spread, each articulation between two elementary modules is an articulation pivoting about an axis of articulation extending in the main plane; this pivoting being obtained by bending (or folding) of the flexible strip of the flexible articulation, or obtained by pivoting between two discrete angles of inclination of the semi-rigid articulation.

The present disclosure also relates to a near-infrared spectroscopy system, comprising a physiological sensor according to the present disclosure, and further comprising a control unit configured to establish the spatial coordinates of each emitter and of each receiver according to the angles of inclination of the articulations, wherein said control unit is connected, on the one hand, to the emitters of the physiological sensor to activate said emitters in an individual and non-concomitant manner, according to a predefined sequence and, on the other hand, to the receivers of the physiological sensor for a recovery and a three-dimensional treatment of the measurements originating from the receivers during said sequence according to the spatial coordinates of the emitters and of the receivers, and wherein the control unit is connected to each angle sensor to establish the spatial coordinates of each emitter and of each receiver according to the measurement data originating from said angle sensors.

Such a spectroscopy system is particularly suitable for all portions of the body, including the limbs and the internal organs (such as the heart) thanks to the conformation of the physiological sensor, and thanks to the control unit which allows activating the emitters according to a predefined sequence and recovering the measurements originating from the receivers. At each activation of an emitter, the control unit will take into consideration some emitters (such as for example pairs of emitters aligned with the activated emitter) and will not take into account some other emitters (in particular those located beyond a predefined threshold distance). Thus, it will be possible to crisscross an examination area at different depths, with a particularly fine resolution. The treatment of the measurements originating from the receivers is called three-dimensional treatment to the extent that it provides a result in depth of the analyzed portion of the body.

As examples of three-dimensional treatment, the control unit is configured for a three-dimensional treatment of the measurements originating from the receivers during the sequence according to a spatial subtraction method, or according to a tomography method with contrasts maps establishment, or according to a point cloud reconstruction method.

The spatial subtraction method implements subtractions between measurements originating from selected receivers.

The tomography method is obtained for example by establishing contrasts maps at different wavelengths.

The point cloud reconstruction method, in turn, implements a consideration of all absorption values by each receiver at each wavelength as constituting a cloud of points. Afterwards, a reconstruction algorithm (such as for example a «machine learning» classification algorithm) will allow identifying a coherence in connection with the different homogeneous absorption volumes, in order to enable a graphical representation, in other words, this reconstruction algorithm will be applied to all points acquired over time so as to better distinguish the areas characterized by the measurement technique. A coefficient of certainty could be assigned to the highly repetitive points, which would allow removing ambiguities on the measurement during an acquisition noised by the movement of the patient for example.

According to one feature, the control unit is configured process according to a three-dimensional treatment (for example, according to a spatial subtraction method, a tomography method, or a point cloud reconstruction method), at each activation of an emitter, only measurements originating from receivers selected according to a relative location with respect to said activated emitter established from their spatial coordinates.

Advantageously, in the planar configuration of the optoelectronic spread, the elementary modules are distributed into several rows and into several columns orthogonal to the rows, and the control unit is configured to process according to a spatial subtraction method, at each activation of an emitter, the measurements originating from receivers disposed in the same row and in the same column as said emitter.

As a complement, it is possible to consider the control unit being configured to process according to a spatial subtraction method, at each activation of an emitter, the measurements originating from receivers also disposed in a row and in a column different from those of said emitter.

The present disclosure also relates to a near-infrared spectroscopy method implementing a spectroscopy system according to the present disclosure, said spectroscopy method comprising the following steps:

collection of the measurement data originating from the angle sensors coupled to each articulation;

establishment of the spatial coordinates of each emitter and of each receiver according to the measurement data originating from the angle sensors (being recalled that these measurement data are dependent of representative of the angles of inclination of the articulations);

activation of the emitters in an individual and non-concomitant manner according to a predefined sequence;

recovery and three-dimensional treatment (for example, according to a spatial subtraction method, a tomography method, or a point cloud reconstruction method) of the measurements originating from the receivers during said sequence according to the spatial coordinates of the emitters and of the receivers.

As previously described, it is possible to consider that the three-dimensional treatment of the measurements originating from the receivers during the sequence implements a spatial subtraction method, or a tomography method with contrasts maps establishment, or a point cloud reconstruction method.

In another variation, the recovery and treatment step is followed by a step of constructing a three-dimensional image representing the underlying tissue strata, and in particular a vascular or blood volume within an analysis volume, said vascular or blood volume being composed of voxels constructed from the three-dimensional treatment of the measurements originating from the receivers during the sequence.

It should be noted that the activation step and the recovery and treatment step are repeated at successive time intervals, in order to enable a dynamic treatment over time to monitor an evolution in real-time.

Advantageously, the spatial coordinates establishment step results in the generation of a three-dimensional and virtual optoelectronic imprint of the physiological sensor in place.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which:

FIG. 1b is a schematic front view of an elementary module of the first physiological sensor of FIG. 1a;

FIG. 2b is a schematic front view of an elementary module of the second physiological sensor of FIG. 2a;

FIG. 3b is a schematic front view of an elementary module of the third physiological sensor of FIG. 3a;

FIG. 8b is a schematic front view of an elementary module of the fourth physiological sensor of FIG. 8a;

FIG. 9b is a view zoomed on the area IX of FIG. 9a;

FIG. 9c is a schematic perspective view of an elementary module of the fifth physiological sensor of FIG. 9a.

Figure 1A:
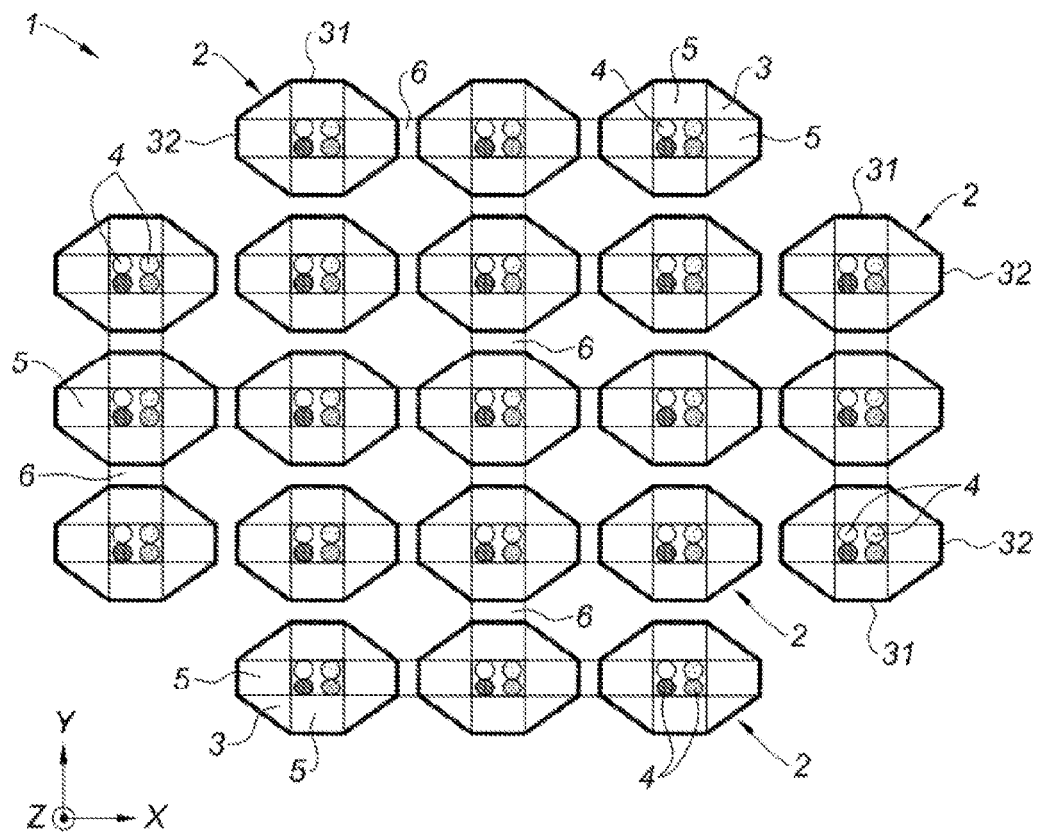
FIG. 1a is a schematic front view of a first physiological sensor in accordance with the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

FIGS. 1a, 1b, 2a, 2b, 3a, 3b, 8a, 8b, 9a, 9b, 9c and 10 schematically represent six variations of a physiological sensor 1 in accordance with the present disclosure, for a near-infrared spectroscopy at different depths. For the rest of the description, the same reference numerals will be used to describe the same structural or functional elements associated with the physiological sensor 1.

In general, the physiological sensor 1 comprises a plurality of elementary modules 2 (or elementary optoelectronic modules) connected together so as to form a flexible or articulated optoelectronic spread.

A physiological sensor 1 may comprise at least ten elementary modules 2, and in particular at least twenty elementary modules 2; the number of elementary modules 2 being related to the surface area of the area to be analyzed.

Each elementary module 2 is provided with a (rigid or flexible) support 3, at least partially made of a rigid or flexible material, such as a plastic, polymeric, elastomeric, composite or metallic material.

This elementary module 2 further comprises at least one optoelectronic component of the near-infrared beam emitter 4 type and/or of the near-infrared photosensitive receiver 5 type, in other words the elementary module 2 comprises:
  at least one near-infrared beam emitter 4; or
  at least one near-infrared photosensitive receiver 5; or
  at least one near-infrared beam emitter 4 and at least one near-infrared photosensitive receiver 5.

Figure 8A:
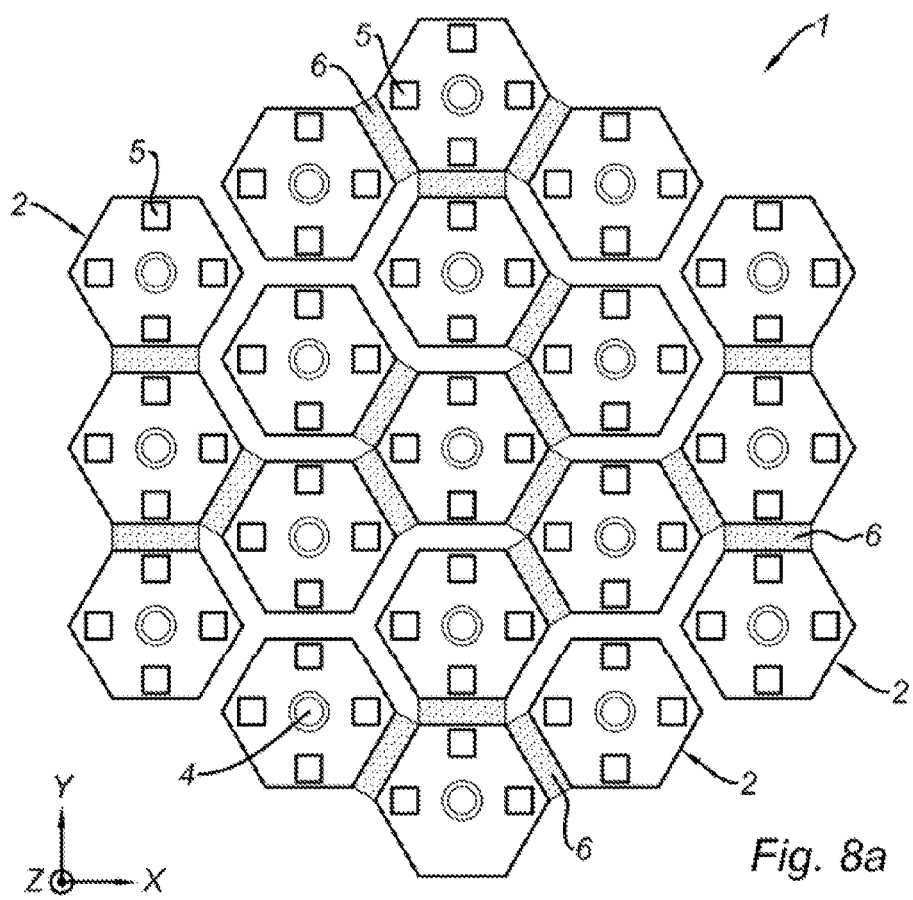
FIG. 8a is a schematic front view of a fourth physiological sensor in accordance with the present disclosure.
Figure 8B:
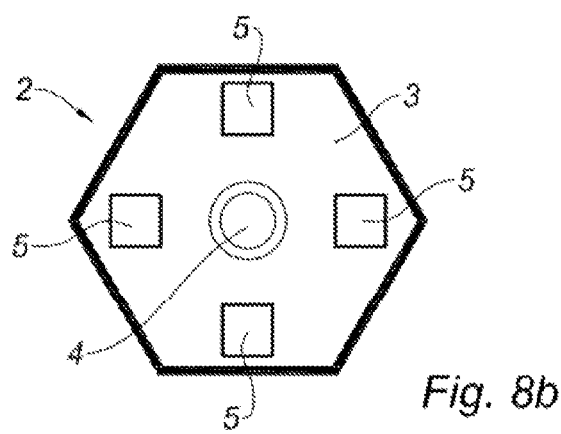

The support 3 may have a polygonal general shape, and in particular a triangular, square, rectangular, hexagonal, octagonal shape, etc. In the examples illustrated in FIGS. 1a to 3b, the support 3 has an octagonal general shape. In the example of FIGS. 8a and 8b, the support 3 has a hexagonal general shape.

Each support 3 of an elementary module is connected to the support 3 of at least one adjacent elementary module by means of an articulation 6 between the two supports 3.

Figure 5A:
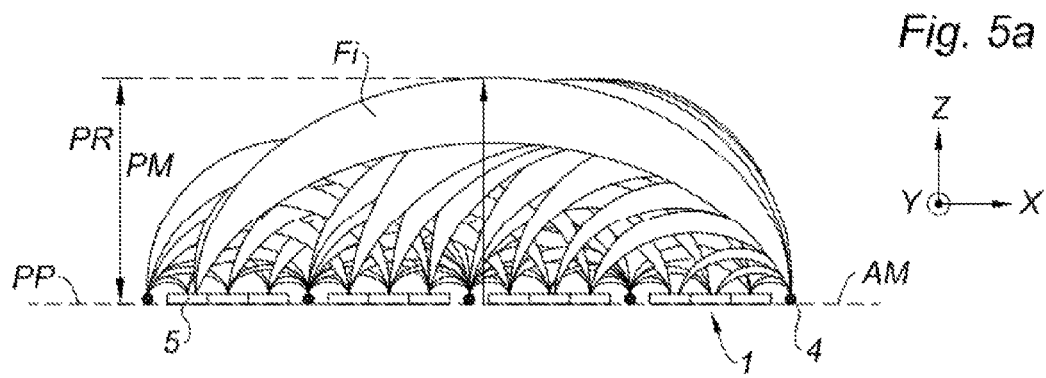
FIG. 5a is a schematic side view of a physiological sensor in accordance with the present disclosure in a planar conformation, with the illustration of near-infrared beams.
Figure 5B:
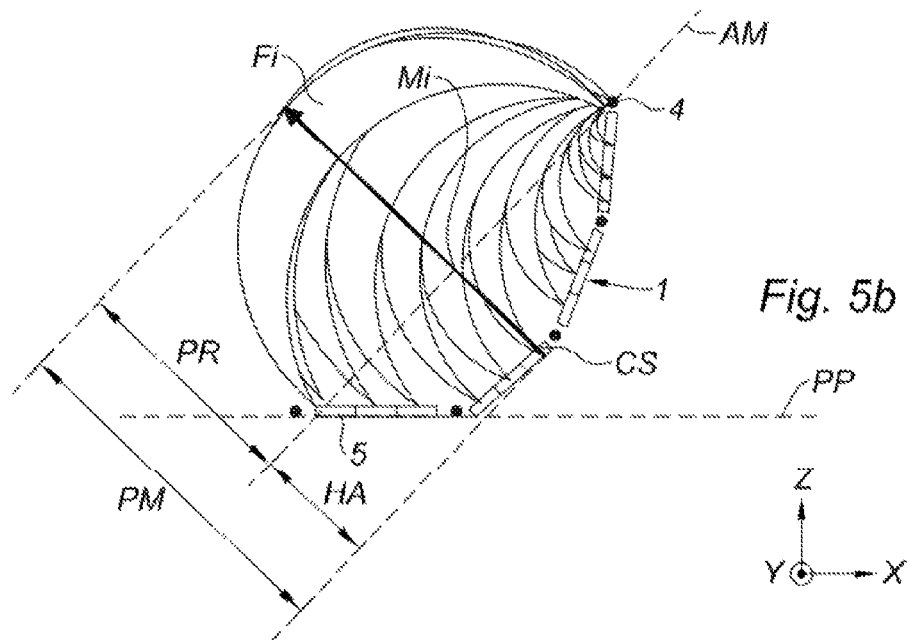
FIG. 5b is a schematic side view of the physiological sensor of FIG. 5a in a curved conformation, with the illustration of near-infrared beams.

Thus, the supports 3 of the elementary modules 2 are assembled or joined by the articulations 6 so that the physiological sensor 1 forms an optoelectronic spread configurable between:
  a planar configuration (illustrated in FIG. 5a) according to a main plane PP in which each articulation 6 has a zero angle of inclination with respect to this main plane PP; and
  a multiplicity of curved conformations (one of which is illustrated in FIG. 5b) in which at least one of the articulations 6 has a non-zero angle of inclination with respect to the main plane PP.

In the planar configuration of the physiological sensor 1 (or of the articulated optoelectronic spread), each articulation 6 is an articulation pivoting about an axis of articulation extending in the main plane PP.

Figure 2A:
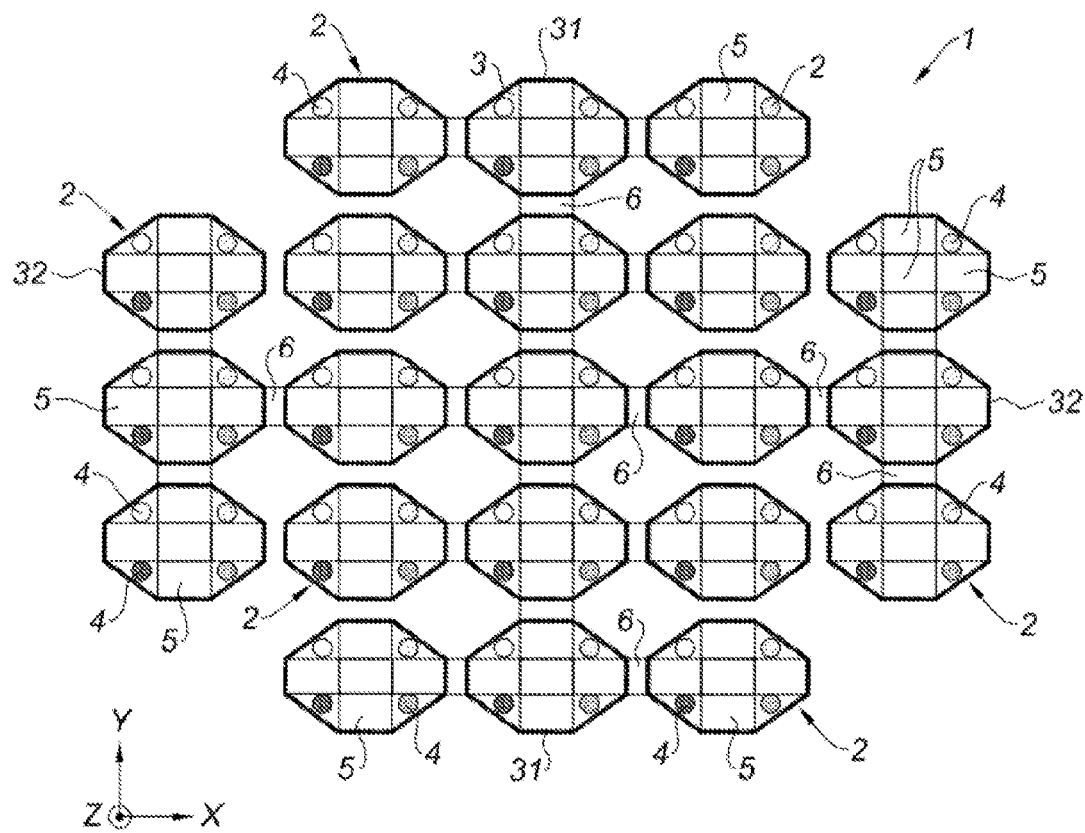
FIG. 2a is a schematic front view of a second physiological sensor in accordance with the present disclosure.
Figure 3A:
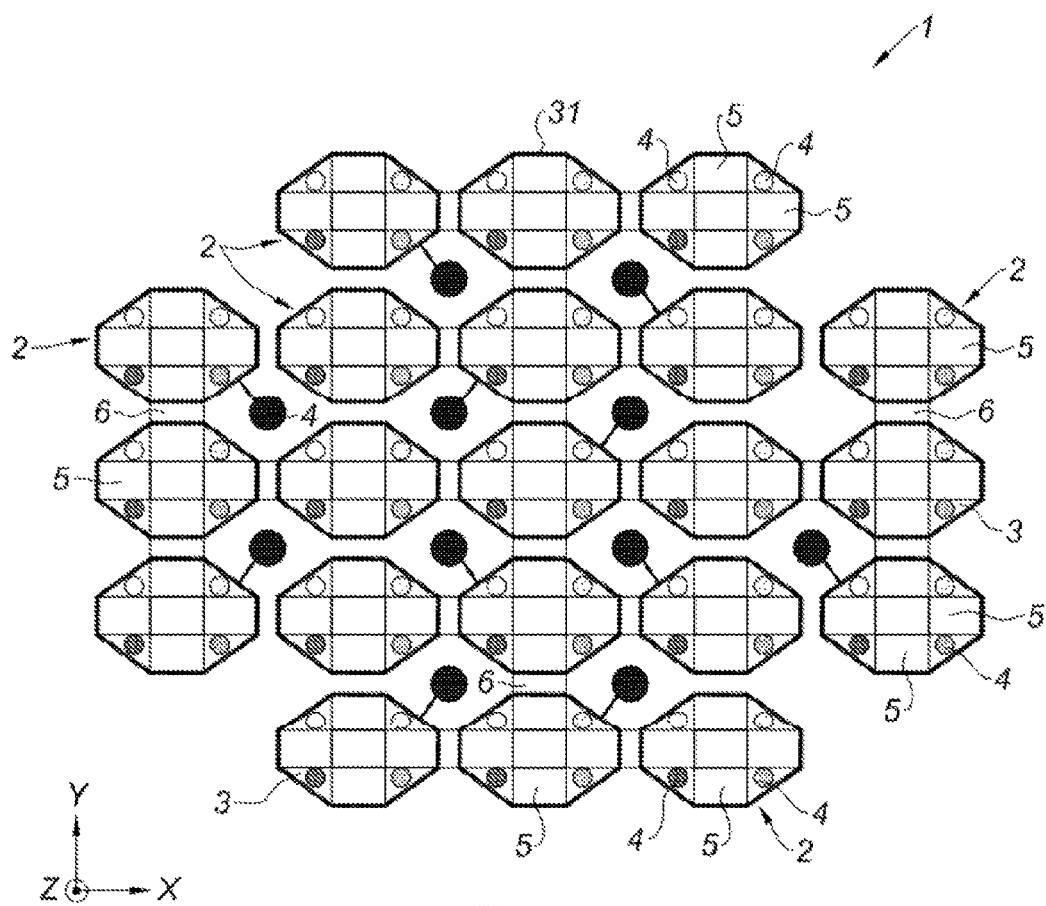
FIG. 3a is a schematic front view of a third physiological sensor in accordance with the present disclosure.

In FIGS. 1a, 2a and 3a, the main plane PP corresponds to the plane (X, Y) defined by a longitudinal axis X and a transverse axis Y orthogonal to the longitudinal axis X; there is also represented a vertical axis Z orthogonal to the main plane PP or (X, Y).

In a first variation, each articulation 6 is a flexible articulation comprising a flexible strip joining the concerned two supports 3, wherein the flexible strip is adapted to bend and thus to enable a continuous adjustment of the angle of inclination between the two supports 3; this adjustment being continuous in the sense that the angle of inclination can vary continuously, that is to say non-discretely, by bending (or folding) of the flexible strip. Such a flexible strip is at least partially made of a flexible material and in particular of an elastomer. Thus, this flexible articulation 6 is pivoted by bending or folding of the flexible strip, which bends about a bending line (or fold line) which forms the axis of articulation.

Thus, in this first variation, the physiological sensor 1 naturally conforms to the portion of the body of the patient. In other words, this physiological sensor 1 bears on a flexible or flexible spread (or matrix) of elementary modules 2 that can conform to the portion of the body of the patient to be analyzed, and in particular to the cutaneous surface as well as to the morphology of the underlying organ.

In the context of this first variation, it is possible to provide a variation in which all or part of the optoelectronic components 4, 5 are integrated into the same flexible membrane 300 which will form a common support for all optoelectronic components 4, 5.

Figure 9A:
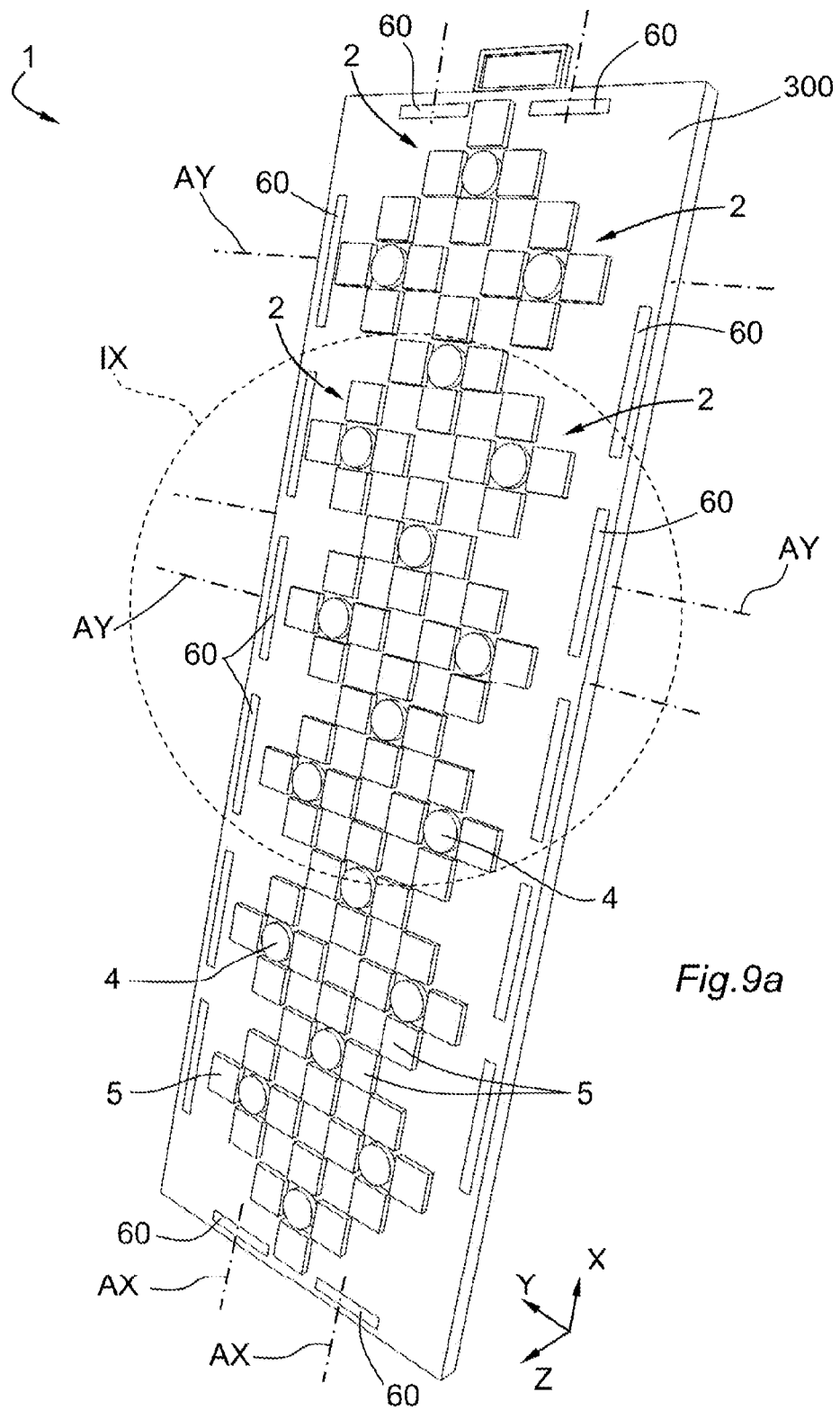
FIG. 9a is a schematic perspective view of a fifth physiological sensor in accordance with the present disclosure.
Figure 9B:
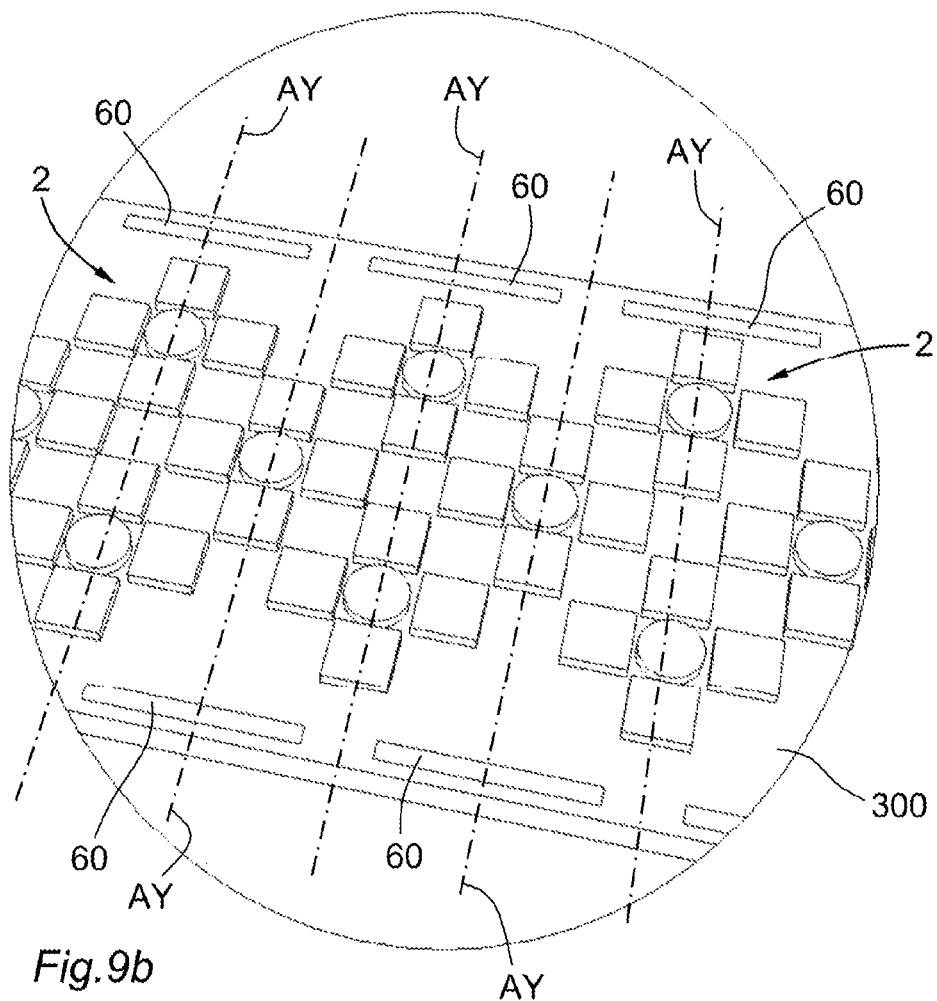
Figure 9C:
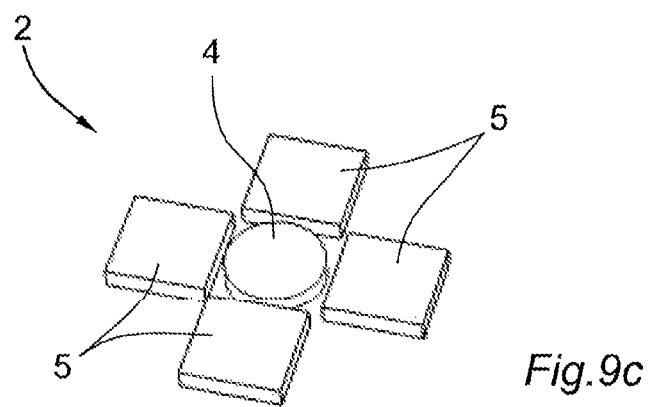
Figure 10:
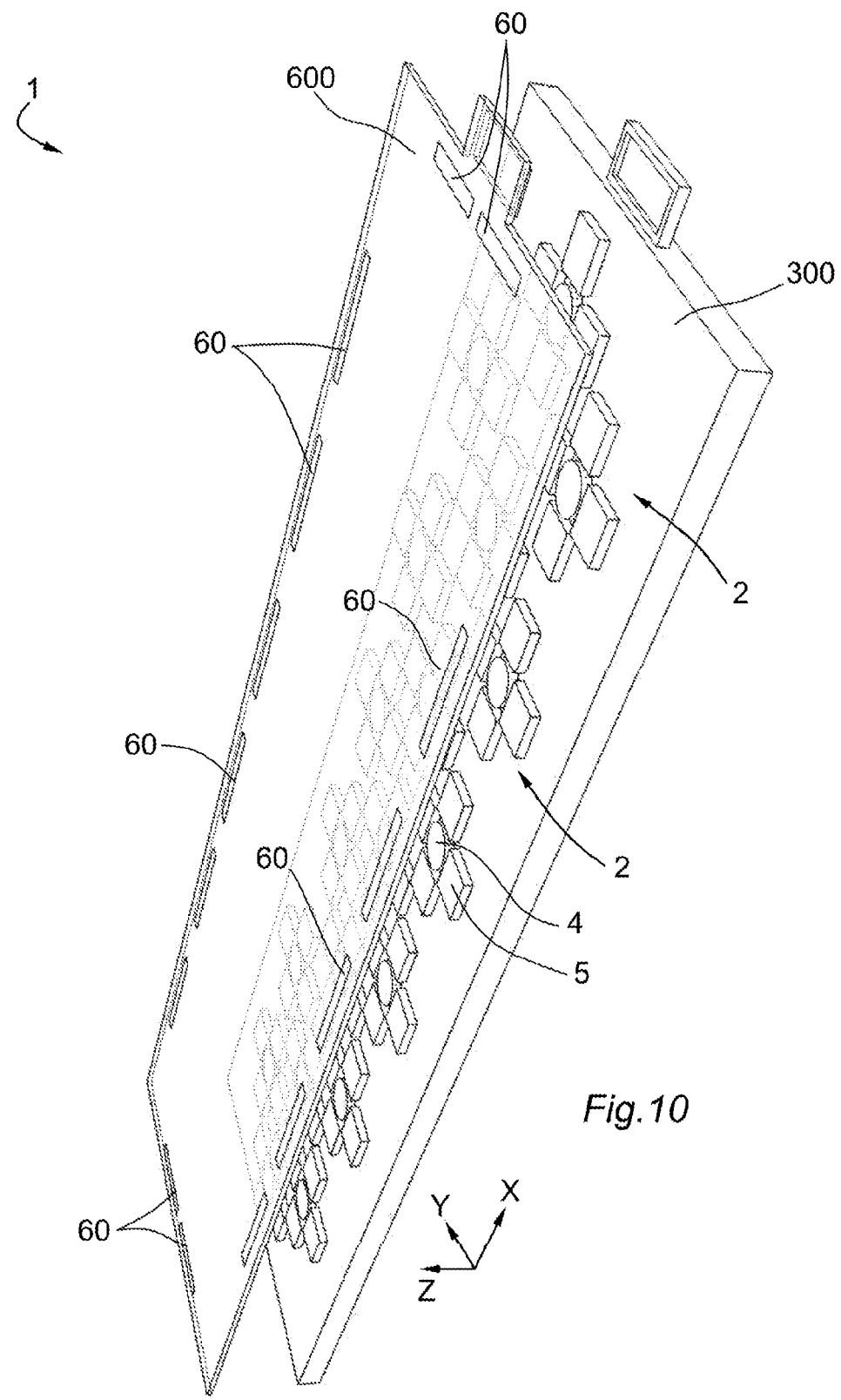
FIG. 10 is a schematic perspective view of a sixth physiological sensor in accordance with the present disclosure.

Such a variation with a flexible membrane 300 is illustrated as examples in FIGS. 9a to 9c with the fifth physiological sensor 1 and in FIG. 10 with the sixth physiological sensor 1. In this variation, the physiological sensor 1 comprises a flexible membrane 300 on which the optoelectronic components 4, 5 are disposed and distributed in islets delimiting the elementary modules 2, wherein the flexible membrane 300 may comprise at least one elastomeric polymer layer in which the optoelectronic components 4, 5 are at least partially embedded. In this case, the flexible strips of the flexible articulations correspond to the portions of the flexible membrane 300 located between the islets delimiting the elementary modules 2, and the supports of the elementary modules 2 correspond to the islets or portions of the flexible membrane 300 on which the optoelectronic component(s) 4, 5 are disposed.

In a second variation, each articulation 6 is a semi-rigid articulation which authorizes several angles of inclination, such that the angle of inclination between two supports 3 is discretely adjustable by determined stages or steps of angles of inclination. Thus, a semi-rigid articulation 6 is configured to maintain a stable inclination between two supports 3 at the discrete angles of inclination provided by this semi-rigid articulation 6. Furthermore, a semi-rigid articulation 6 can tilt between two distinct angles of inclination under the effect of a force applied on at least one of the concerned two supports 3, in particular when the physiological sensor 1 is pressed or applied on the portion of the body of the patient to be analyzed.

Thus, in this second variation, the physiological sensor 1 naturally conforms to the portion of the body of the patient, none the less noting that the angles of inclination between the supports 3 will correspond to the discrete angles of inclination. In other words, this physiological sensor 1 bears on an articulated spread (or matrix) of elementary modules 2 which can conform to the portion of the body of the patient to be analyzed, and in particular to the cutaneous surface as well as to the morphology of the underlying organ.

It should be noted that each elementary module 2 is connected to at least one adjacent (or neighboring) elementary module 2 via an articulation 6. One or several elementary module(s) 2 may be connected to four adjacent elementary modules 2, in particular for the elementary modules 2 disposed in the central portion of the physiological sensor 1. Other elementary modules 2 may be connected to one, two or three adjacent elementary modules 2, in particular for the elementary modules 2 disposed at the border of the physiological sensor 1. The arrangement of the articulations 6 will depend in particular on the targeted applications, and in particular on the shape and the extent of the area to be analyzed.

As shown in FIGS. 1a, 2a, 3a, 8a, 9a and 10, in the planar configuration of the physiological sensor 1 (or of the optoelectronic spread), the elementary modules 2 are distributed into:
- several rows parallel to the longitudinal axis X; and into
- several columns parallel to the transverse axis Y and therefore orthogonal to the rows.

In the examples of FIGS. 1a to 3b, each support 3 comprises:
- two opposite longitudinal edges 31 parallel to the longitudinal axis X; and
- two opposite transverse edges 32 parallel to the transverse axis Y.

The shapes, dimensions and arrangements of the supports 3 may vary depending on the targeted applications, and in particular depending on the portions of the body or the concerned organs (heart, arm, skull, leg, etc.), and also on the types of patients (adult, child, baby, man, woman). Recall that in the variations of FIGS. 9a to 9c and 10, the support is common to the optoelectronic components 4, 5 and is made in the form of a flexible membrane 300.

Each articulation 6 connects:
- either two transverse edges 32 contiguous to two adjacent respective supports 3, with an axis of articulation parallel to the transverse axis Y;
- or two longitudinal edges 31 contiguous to two adjacent respective supports 3, with an axis of articulation parallel to the longitudinal axis X.

In the examples of FIGS. 8a and 8b, each support 3 comprises six edges, and each articulation 6 connects two edges contiguous to two adjacent respective supports 3.

Thus, the articulations 6 between the elementary modules 2 enable the continuous (or almost continuous) contact of the emitters 4 and receivers 5 with the examination surface, without the creation of an intermediate air layer which would be a source of luminous diffusion.

In the above-described first variation wherein the articulations 6 are flexible articulations, each flexible articulation 6 forms a flexible hinge which contributes in conforming naturally to the shape or contour of the portion of the body to be analyzed.

The flexible strip of each flexible articulation 6 may be adjustable in a continuous manner and by bending, between an angle of −30 degrees (bending in a first direction with respect to the main plane PP) and an angle of +30 degrees (bending in a second direction with respect to the main plane PP), wherein these bending maximums at −30 and +30 degrees correspond to bending limits specific to the flexible strip. Of course, these bending maximums at −30 and +30 degrees may be larger in absolute value. As example, with a total angulation of 30° between two supports 3, three aligned supports 3 can provide the physiological sensor 1 with an angle of 90°. These angular characteristics are likely to be different depending on the design and the targeted applications.

In the above-described second variation wherein the articulations 6 are semi-rigid articulations, each semi-rigid articulation 6 may be provided with notches for setting the angle of inclination between the two supports 3 according to several predefined values, for a natural adjustment, during the application on the portion of the body of the patient to be analyzed, in a discrete manner by determined angle of inclination stages or steps. Thus, each semi-rigid articulation 6 forms a notched hinge, wherein one angle of inclination corresponds to each setting notch.

Each semi-rigid articulation 6 may be adjustable according to several predefined angles of inclination comprised between 0 degrees and 30 degrees, with a separation by one constant angular step (or stage), in particular an angular step comprised between 5 and 15 degrees. With a total angulation of 30° between two supports 3, three aligned supports 3 may provide the physiological sensor 1 with an angle of 90°. These angular characteristics are likely to be different depending on the design and the targeted applications.

For example, each semi-rigid articulation 6 may have the following angles of inclination, in degrees, [0, 5, 10, 15, 20, 25, 30] or [0, 10, 20, 30] or [0, 15, 30].

Each semi-rigid articulation 6 is also provided with two stops for stopping the inclination between a minimum value and a maximum value, for example between 0 degrees and 30 degrees or between −30 and +30 degrees.

In order to automatically determine the angle of inclination, among the different offered discrete values, each articulation 6 (whether it is flexible or semi-rigid) between two supports 3 is coupled to an angle sensor (not illustrated in FIGS. 1a to 3a and 8a, 8b, and on the contrary illustrated in FIGS. 9a, 9b and 10) configured for the measurement of the angle of inclination between the two supports 3.

In the first variation, the angle sensor is in the form of a flexible resistive sensor outputting a measurement datum reflecting a variation of resistance as a function of the bending of the flexible strip. Such a flexible resistive sensor, or bending sensor, allows measuring the angle of inclination between the two supports 3 (which corresponds to the bending angle of the flexible strip) based on the exploitation of the resistance variations occurring when a conductive material is curved. Thus, the flexible resistive sensor behaves as a passive potentiometer whose resistance varies as a function of the bending.

Such a flexible resistive sensor may be:
- either integrated to the flexible strip,
- or integrated to a flexible bladed fastened to the flexible strip, in particular in a detachable manner (for example by gluing, adhesive, magnetization, clipping, pressing, . . . ) so that a bending of the flexible strip results in a bending of the flexible blade, and therefore to a bending of the conductive material of the flexible resistive sensor.

In the context of the first variation with the flexible membrane 300, two distinct realizations may be considered for the integration of resistive sensors 60.

In the variation of FIGS. 9a and 9b, the flexible resistive sensors 60 are integrated to the flexible membrane 300, by being for example embedded at least partially in an elastomeric polymer layer.

Such resistive sensors 60 may be disposed between the islets delimiting the elementary modules 2.

Alternatively, for reasons related to bulk in particular, and as shown in FIGS. 9a and 9b, the resistive sensors 60 may be offset on the sides of the flexible membrane 300, by disposing resistive sensors 60 along the articulation axes AX, AY, so that the resistive sensors 60 could measure bendings at the level of the flexible strips along the corresponding articulation axes. In the example of FIGS. 9a and 9b, the resistive sensors 60 that measure bendings according to articulation axes AY, parallel to the direction Y, are distributed in an alternate manner between the two longitudinal sides (sides according to the direction X) of the flexible membrane 300. Hence, it should be noted that one resistive sensor 60 can be coupled to two articulations or more.

In the variation of FIG. 10, the flexible resistive sensors 60 are integrated to a flexible film 60 which is attached and fastened (in particular in a removable manner) on the flexible membrane 300, with the flexible resistive sensors which may be either superimposed with the flexible strips which, as a reminder, correspond to the portions of the flexible membrane located between the islets delimiting the elementary modules 2, or offset on the sides of the flexible film 600 according to the same offset shape as in FIGS. 9a and 9b.

If the flexible film 600 is positioned on the front of the flexible membrane 300 and covers the optoelectronic components 4, 5, then this flexible film 600 is necessarily transparent. On the contrary, if the flexible film 600 is positioned on the rear of the flexible membrane 300, then this flexible film 600 may be opaque or transparent.

Thus, the flexible membrane 300 with its optoelectronic components 4, 5 may be intended for one single use or not. Similarly, the flexible film 600 with its flexible resistive sensors 60 may be intended for one single use or be reusable independently of the flexible membrane 300.

In the second variation, the angle sensor is shaped for example so as to detect the occupied setting notch in the semi-rigid articulation 6, this setting notch may then be associated with an angle of inclination. For example, this angle sensor may comprise contactors coupled to each setting notch.

As a non-limiting example, each semi-rigid articulation 6 may comprise:

several retractable balls cooperating with an elastic thrust element, such as a spring or a flexible or elastic blade, wherein these balls are inserted into a curved rail with a curvature corresponding to the desired maximum angle of inclination sector and this rail is slidable mounted inside a guide with the same curvature, and a cursor on the guide adapted to crush the balls according to the sliding of the rail within the guide, wherein the supports 3 linked by the articulation 6 are fastened respectively to one end of the rail and to one end of the guide;

stops which inhibit the rail and the guide from disengaging from each other, while blocking the inclination between a minimum value and a maximum value.

Alternatively to the cursor, it may be considered to provide for recess forming notches on the rail, thereby releasing the pressure on the balls.

It should be noted that the articulations 6 may possibly be the supports of the connection cables for the emitters 4 and the receivers 5 and/or the location of flexible electrical connections linking two elementary modules 2.

In general, for each elementary module 2, all of the optoelectronic component(s) 4, 5 are mounted on a front face of the concerned support 3, this front face corresponding to the face that is applied on the portion of the body to be analyzed. Thus, the support 3 has a front face, as well as back face opposite to the front face, this back face being thus opposed to the portion of the body to be analyzed.

It may also be considered that for each elementary module 2, the optoelectronic component(s) 4, 5 are covered with a layer of a transparent material.

Figure 1B:
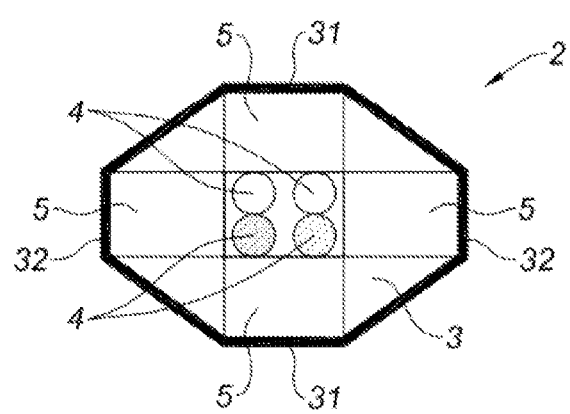

In the first variation of FIGS. 1a and 1b, each elementary module 2 comprises, on its support 3, four emitters 4 emitting at distinct lengths in the near-infrared between 650 and 1000 nanometers, as well as four receivers 5.

The four emitters 4 are placed at the center of the support 3 and the four receivers 5 are placed at the periphery of the support 3, around the four receivers. In the spatial subtraction calculations, and in general in the three-dimensional treatment of the data originating from the receivers 5, the four emitters 4 thus grouped together may possibly be associated with a common spatial coordinate.

Two receivers 5 are disposed on either side of the emitters 4 according to a longitudinal direction parallel to the longitudinal axis X, so that these two receivers 5 are shifted axially according to this longitudinal direction, contributing in increasing the spectroscopic resolution in longitudinal direction by multiplying the receivers 5.

Similarly, two other receivers 5 are disposed on either side of the emitters 4 according to a transverse direction parallel to the transverse axis Y, so that these two other receivers 5 are shifted axially according to this transverse direction, also contributing in increasing the spectroscopic resolution in transverse direction by multiplying the receivers 5.

Figure 2B:
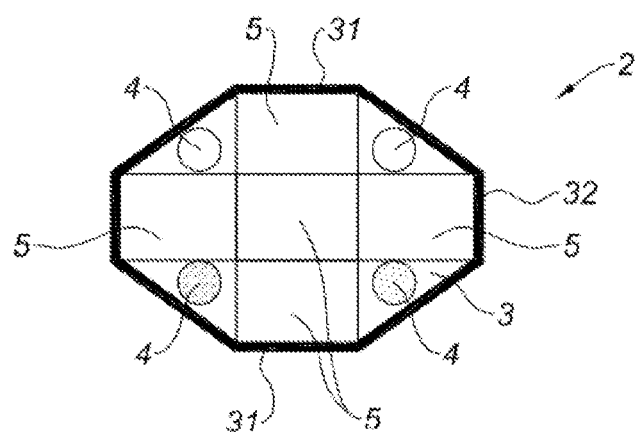

In the second variation of FIGS. 2a and 2b, each elementary module 2 comprises, on its support 3, four emitters 4 emitting at distinct lengths in the near-infrared between 650 and 1000 nanometers, as well as five receivers 5.

A receiver 5, called central receiver, is placed at the center of the support 3 and the four other receivers 5 are placed at the periphery of the support 3, around the central receiver 5.

Two receivers 5 are disposed on either side of the central receiver 5 according to a longitudinal direction parallel to the longitudinal axis X, so that these two receivers 5 and the central receiver 5 are shifted axially according to this longitudinal direction, contributing in increasing the spectroscopic resolution in longitudinal direction by multiplying the receivers 5.

Similarly, two other receivers 5 are disposed on either side of the central receiver 5 according to a transverse direction parallel to the transverse axis Y, so that these two other receivers 5 and the central receiver 5 are shifted axially according to this transverse direction, also contributing in increasing the spectroscopic resolution in transverse direction by multiplying the receivers 5.

The four emitters 4 are placed at the four corners of the support 3 between the four receivers 5 disposed at the periphery.

Figure 3B:
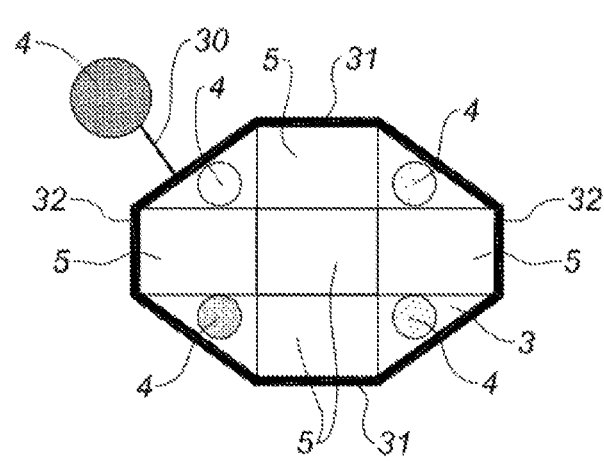

In the third variation of FIGS. 3a and 3b, each elementary module 2 is identical to the elementary module 2 of the second variation, with the difference that some of the elementary modules 2 support another emitter 4 (and else possibly another receiver) which is carried by the support 3 via an arm 30 so that said other emitter 4 (or receiver) is disposed in an interstitial area between four neighboring elementary modules 2.

This solution with emitter 4 (or receiver) held by an arm would have also been considerable with the elementary module 2 of the first variation.

It would have also been possible to consider providing on some elementary modules 2 only one or several emitter(s) 4, and providing on the other elementary modules 2 only one or several receiver(s) 5.

Depending on the desired sizes of the emitters 4 and of the receivers 5, which form optoelectronic components, and depending on the targeted applications, it may be considered to have several solutions:

a uniform combination of optoelectronic components (emitters and receivers), whether homogeneous or heterogeneous, forming a subset;

simple unitary optoelectronic components, emitters and receivers;

a mixed combination of the two previous solutions.

The emitters 4 may consist of off the shelf emitters, they may consist of optical fibers coupled to an infrared source, laser diodes, light-emitting diodes or else optoelectronic components manufactured in clean room. For example, the emitters 4 may be constituted by diodes of different sizes, combining large-size and small-size diodes.

The receivers 5 may consist of CMOS sensors, photodiodes, photoresistors, phototransistors, photocells or else optoelectronic components manufactured in clean room.

In the case of elementary modules 2 comprising at least one emitter 4, it is possible to consider having several emitters 4 having different wavelengths. These emitters 4 are then advantageously grouped together, in particular at the center of the support 3, in order to be considered during the treatment as one single light source. Thus, these emitters 4 behave as one single light source with multiple wavelengths. The choice and the number of the wavelengths depend on the targeted applications, and in particular the targeted metabolites and molecules.

By its capacity to conform to the morphology of an organ or of a portion of the body, the physiological sensor 1 enables in particular the monitoring of the perfusion of a wide range of organs or portions of the body.

Thus, such a physiological sensor 1 may be considered, for its conformability, to monitor the tissue perfusion of various subcutaneous areas, including the frontal cortex, but also the kidneys, the mesentery, and the muscles. This physiological sensor 1 may also be considered, for its conformability and under sterile conditions, to monitor the perfusion of organs during a surgery, such as the myocardial muscle during a cardiac surgery.

Indeed, the articulations 6 of this physiological sensor 1 allow circumventing the morphological obstacles of the application or measurement surface, including the creation of diffusive air layers. These articulations 6 also allow reducing the optical path length inside the biological tissues, while gaining more measurement depth, by using the relief and sometimes the roundness of their shape. In a particular configuration, the physiological sensor 1 may be configured and positioned in a half circle arc fashion so that optoelectronic components 4, 5 may be aligned opposite each other on either side of the organ or the portion of the body.

In the context of a near-infrared spectroscopy system, such a physiological sensor 1 is used in association with a control unit (not illustrated) such as a computer terminal, a controller, a microcontroller, a processor, a microprocessor, an electronic board, a data acquisition and processing board, or any other assembly of electronic components suitable for the implementation of the functions set out hereinafter.

The control unit is thus connected, in a wired or wireless way, to the emitters 4, to the receivers 5 and to the angle sensors of the articulations 6. Each emitter 4 and each receiver 5 is addressed individually by the control unit.

In the case of a wired way, a cables bundle connects the control unit to the emitters 4, receivers 5 and to the angle sensors, without impeding the mobility of the physiological sensor 1. Preferably, the cabling is located at the back of the elementary modules 2 (that is to say over the back face of the support 3) in order not to reduce the useful surface area of the physiological sensor 1 (that is to say the surface area of the front faces of the supports 3).

In the case of a wireless way, cables connecting the emitters 4, receivers 5 and angle sensors to a radio-communication system carried by the physiological sensor 1, for example at the back of an elementary module 2 (in other words over a back face of a support 3) or else on a dedicated support 3 which does not necessarily carry any emitter 4 and receiver 5. This radio-communication system is in bidirectional radio-communication with the control unit in order to send and receive data.

For example, the radio-communication system may comprise a short-range radio-communication chip (for example with a maximum range comprised between one and five meters, or else fifteen meters) according to a WBAN «Wireless Body Area Network» or WBASN «Wireless Body Area Sensor Network» technology, in order to be able to establish a radio-communication over a WBAN or WBASN network between the physiological sensor 1 and the control unit. As a non-limiting example, among the different WBAN or WBASN technology protocols, the Zigbee™ and Bluetooth™ Low Energy (BLE) protocols may be retained.

The control unit is configured to fill several functions including mainly the four functions described hereinafter, in order words to carry out several steps.

A first function of the control unit (or a first step) is the establishment of the spatial coordinates of each emitter 4 and of each receiver 5 according to:
the angles of inclination of the articulations 6;
the positioning of the corresponding elementary module 2 in the physiological sensor 1 (for example $3^{rd}$ row and $1^{st}$ column);
the positioning of the emitter 4 or receiver 5 within the corresponding elementary module 2 itself.

These spatial coordinates are established once the physiological sensor 1 is applied on the portion of the body of the patient to be analyzed, and therefore once the physiological sensor 1 is in the adequate curved conformation. The angle sensor of each articulation 6 communicates, to the control unit, the value of the angle of inclination or the index of the setting notch or the value of the resistance of the passive potentiometer (depending on the retained technology) which is translated by the control unit into an angle of inclination.

This first function may be repeated in an iterative or regular manner, in order to dynamically determine these spatial coordinates. Indeed, the portion of the body of the patient to be analyzed may evolve in its shape and in its size, such as for example by swelling or deflating, and in this case the curved conformation of the physiological sensor 1 changes and therefore the spatial coordinates change. In other words, a command from the control unit actualizes at each cycle (a cycle corresponding to the completion of the mentioned four functions or steps) the information relating to the angles of inclination. Thus, the three-dimensional representation of the physiological sensor 1 is actualized at each measurement cycle within the orthonormal reference frame (X, Y, Z) of the measurement volume.

Thus, each emitter 4 and each receiver 5 are located by their coordinates in the same orthonormal reference frame (X, Y, Z), in the same virtual space in three dimensions as that of the analyzed body or tissues.

Thus, the control unit allows constructing a three-dimensional and virtual optoelectronic imprint of the physiological sensor 1 in place on the organ or on the portion of the body, and this three-dimensional optoelectronic imprint is placed in the orthonormal reference frame (X, Y, Z), as shown in FIGS. 5a and 5b, to serve in the analysis of the signals measured by the receivers 5, and therefore in the graphical representation of the analyzed volumes under the physiological sensor 1, as explained later on.

The discrimination of the different biological planes under the physiological sensor 1, according to their vascularization, allows spotting the area to be examined. This area to be examined may be defined by its three-dimensional optoelectronic imprint at the wavelength of 800 nanometers for example, in order to represent the measurement volume.

A second function (or a second step) is the activation of the emitters 4 in an individual and non-concomitant manner according to a predefined sequence. In other words, the control unit activates the emitters 4 in an alternate manner. The emitters 4 may be synchronized to one another for a chase-like illumination, some after the others, without ever having two emitters 4 being activated at the same time.

A third function (or a third step) is a recovery and a three-dimensional treatment (for example according to a spatial subtraction method) of the measurements originating from the receivers 5 during the sequence according to the spatial coordinates of the emitters 4 and of the receivers 5.

A fourth function (or a fourth step) is the construction of a three-dimensional image representing a vascular or blood volume within an analysis volume, this vascular or blood volume being composed of voxels VO constructed from the three-dimensional treatment, in particular according to a spatial subtraction method, of the measurements originating from the receivers during the sequence.

The data acquisition is based on a spatial and temporal modulation of the infrared emissions. The control unit is capable of acquiring images during the same period, thereby providing the temporal coherence of the acquisition.

The temporal coherence between the emitters 4 and the acquisition by the receivers 5 is the object of a synchronization command which is directly integrated within the control unit. Alternatively, each elementary module 2 directly integrates a synchronization module between the emitters 4 and the receivers 5.

For the implementation of the spatial subtraction method, each different combination of an emitter 4 and of a receiver 5 forms a measurement twosome 4, 5. Each measurement twosome 4, 5 is unique both by:

the measurement axis AM that passes through the emitter 4 and through the receiver 5, and which is assimilated to the axis of the near-infrared beam FI emitted by the emitter 4, passing through the tissues of the portion of the body or of the organ, and received by the receiver 5; and by the spacing (or separating distance) between the emitter 4 and the receiver 5.

Figure 4:
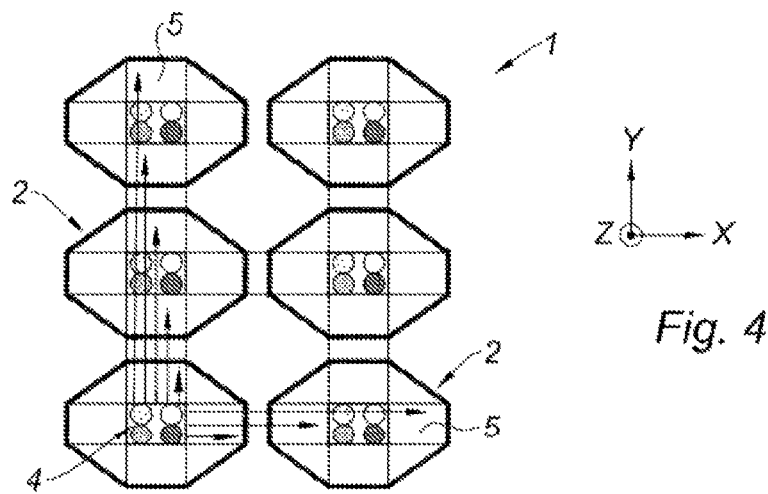
FIG. 4 is a schematic front view of six elementary modules of the first physiological sensor of FIG. 1a, illustrating the near-infrared beams which are taken into consideration during the activation of an emitter.

The absorption value measured at the level of a receiver 5 which results from the activation of an emitter 4 is a unique information on the location of hemoglobins in the tissues crossed by the near-infrared beam FI associated with the concerned measurement twosome 4, 5. FIG. 4 illustrates several measurement twosomes 4, 5 by means of arrows which schematically represent near-infrared beams in eight measurement twosomes 4, 5 all being associated with the same emitter 4, including five measurement twosomes 4, 5 along the transverse axis Y and three measurement twosomes 4, 5 along the longitudinal axis X.

The trajectory of near-infrared beam for a measurement twosome 4, 5 is curvilinear or is in the form of a diffuse light arc which passes through the organic tissues, as schematized in FIGS. 5a and 5b, and its relative depth PR with respect to the measurement axis AM corresponds to about one third of the spacing between the emitter 4 and the receiver 5 of the measurement twosome.

Given the vascular heterogeneity of the crossed tissues, and therefore a heterogeneous light absorption, it is advantageous to operate a series of spatial subtractions in order to make the absorption measurements more selective, and the physiological sensor 1 according to the present disclosure allows addressing this point. Indeed, each emitter 4/receiver 5 separating distance being known, as well as each separating distance between the receivers 5 being also known, all combinations of measurement twosomes 4, 5 having the same emitter 4 are listed by the control unit.

For a spatial subtraction, each emitter 4 is associated with at least one twosome of receivers 5, and preferably several twosomes of receivers 5, for a subtraction of the absorption measurements between the receivers 5 of the same twosome; the twosome(s) of considered receivers 5 associated with the emitter 4 have the same measurement axis, in other words the emitter 4 and the receivers 5 are aligned on the same measurement axis to operate the spatial subtraction.

The emitters 4 and the twosomes of receivers 5 related thereto are synchronized in the same illumination time. All these successive illuminations take place at such speed that they are considered as taking place within the same time frame.

Thus, the optoelectronic imprint constructed during the first step (or with the first function) serves to establish the paired emitters 4 and receivers 5 for the spatial subtractions, all these pairings being singular and unique by their measurement axes (singularity of the optical paths) as well as the separating distances and the angles of inclination to be considered between the biased optoelectronic components 4, 5 of the physiological sensor 1.

Each measurement twosome 4, 5 represents a depth absorption value. It should be noted that the X, Y and Z coordinates of the optoelectronic components 4, 5 are known from their arrangements on the physiological sensor 1 (arrangement of the elementary modules 2 within the physiological sensor 1 and arrangement of the optoelectronic components 4, 5 on their own elementary modules 2) and from the concerned angles of inclination.

Thus, this depth absorption value is associated with a relative depth PR with respect to the measurement axis AM of the measurement twosome 4, 5, and which corresponds to one third of the separating distance between the concerned emitter 4 and receiver 5.

Referring to FIG. 5b, if the physiological sensor 1 has a curvature between the emitter 4 and the receiver 5 of the considered measurement twosome 4, 5, while the relative depth PR is distinct from the measurement depth PM, which corresponds to the penetration depth of the near-infrared beam FI in the portion of the body or of the organ. More specifically, the measurement depth PM corresponds to the sum of the relative depth PR and of the height HA measured orthogonally to the measurement axis AM between:

a middle point MI located on the measurement axis AM, in midway between the emitter 4 and the receiver 5, and the physiological sensor 1, in other words a point of contact CS between the physiological sensor 1 and the cutaneous surface of the portion of the body or of the organ of the patient.

Referring to FIG. 5a, if the physiological sensor 1 is planar between the emitter 4 and the receiver 5 of the considered measurement twosome 4, 5, while the relative depth PR corresponds to the measurement depth PM, in other words the height HA is zero.

During the third step (or with the third function), the spatial subtraction is carried out between all or part of the pairs of measurement twosomes 4, 5 with the same emitter 4 and with receivers 5 aligned according to the same measurement axis AM, by subtracting the least deep signal (that corresponding to the measurement twosome having the smallest separating distance between the emitter 4 and the receiver 5) from the deepest signal (that corresponding to the measurement twosome having the largest separating distance between the emitter 4 and the receiver 6).

Figure 6:
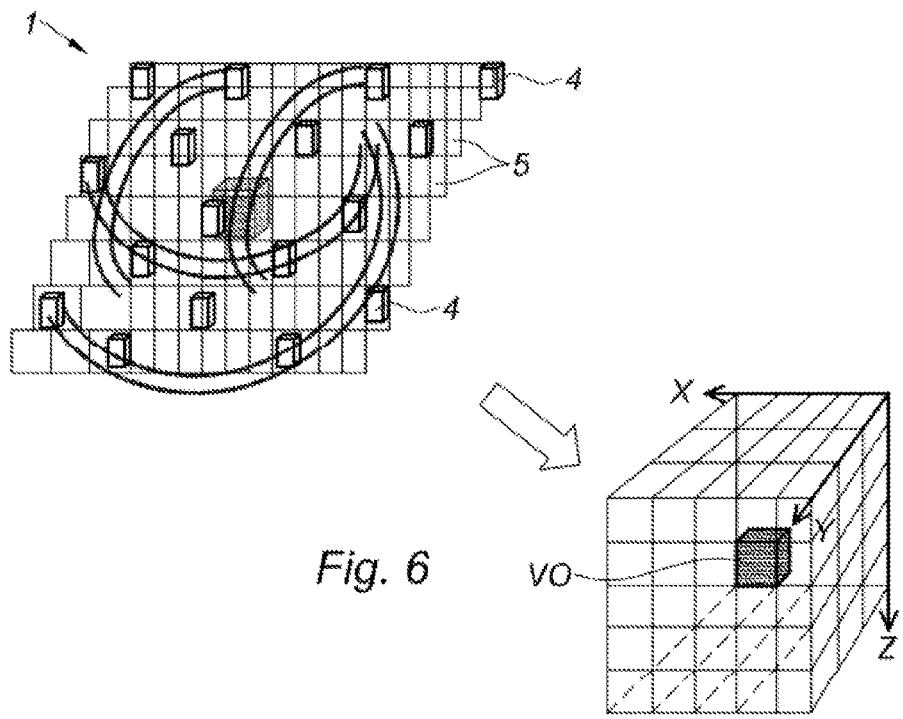
FIG. 6 is a schematic illustration of a spatial subtraction of beams for the construction of a voxel under a physiological sensor in accordance with the present disclosure.
Figure 7A:
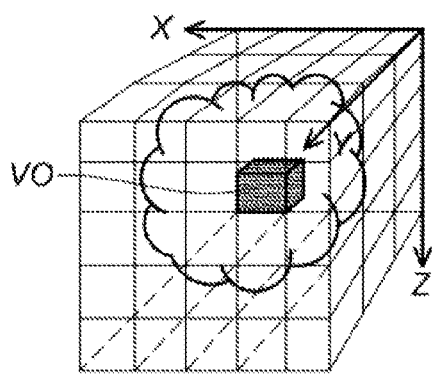
FIGS. 7a and 7b are schematic views of the voxel of FIG. 6 in the case of an imagery of a hematoma type (FIG. 7a) or an artery type (FIG. 7b) blood volume.
Figure 7B:
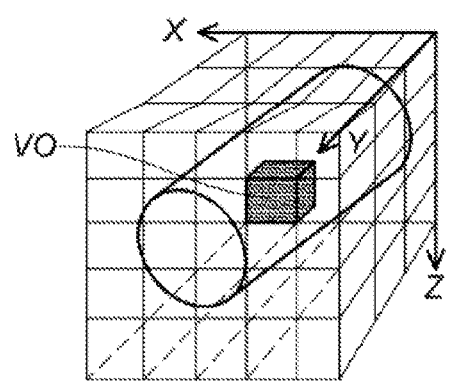

During the fourth step (or with the fourth function), the result of this subtraction between the absorption value of the least deep signal and the absorption value of the deepest signal is associated with X, Y, Z coordinates and is thus logged in a volumetric map in the form of a voxel VO, as schematized in FIG. 6, in FIG. 7a wherein a voxel VO originating from an imagery of a hematoma type blood volume is illustrated, or in FIG. 7b wherein a voxel VO originating from an imagery of a blood vessel type blood volume is illustrated.

The coordinates of the voxel depend on the coordinates of the emitter 4 and of the considered two receivers 5, and therefore depend, amongst other, on the concerned angle(s) of inclination.

As example, if the physiological sensor 1 is planar between the emitter 4 and the considered receivers 5, the measurement axis that passes through the emitter 4 and the aligned receivers 5 will form the reference axis. If the physiological sensor 1 has a curvature between the emitter 4 and the receiver 5 of the considered measurement twosome 4, 5, the bisector of the angle formed by the axes passing through the emitter 4 and the two receivers 5 will form the reference axis.

During this fourth step, reconstruction algorithms, in particular based on photons detection thresholds, may serve to reconstitute a three-dimensional mapping as well as a volumetry of absorption homogeneous areas. The voxels may be crossed with each other to refine the resolution.

A variant to the spatial subtraction method may be a tomography method with contrasts maps establishment, or else a point cloud reconstruction method consisting in considering all absorption values of each receivers 5 at each wavelength to form a point cloud. Afterwards, reconstruction algorithms will focus in identifying the coherence thereof in connection with the different homogeneous absorption volumes, in order to enable a three-dimensional graphical representation.

In a primary and non-limiting manner, the physiological sensor 1 is preferred for medical application regarding the hemodynamics of patients, by implementing wavelengths tuned to hemoglobins such as 803 nanometers, an example of an absorption isosbestic point of hemoglobins, or else wavelengths further tuned to oxygenated and deoxygenated hemoglobins.

Thus, a wavelength close to the isosbestic point of hemoglobins at 803 nanometers may be used to establish a high-contrast three-dimensional map. As hemoglobins circulate only in the vascular network, and the organs, bones and integuments have a variable vascularization, a discrimination of the biological tissues may thus be operated. For example, in the case of the monitoring of the frontal cortex, the physiological sensor 1 allows discriminating the scalp, the cranial cavity, the white matter from the grey matters, each having a different vascular density.

Other wavelengths in the near-infrared, around 800 nanometers may be used for the discriminations of oxygenated hemoglobins from deoxygenated hemoglobins. The optical paths of the light beams of these different wavelengths may then be either considered as similar to those of the wavelength at 800 nanometers, because of their juxtaposition with the latter on the concerned elementary modules 2, or considered with regards to these during the treatment by the reconstruction algorithms. The process of three-dimensional representation of the elementary modules 2 and of the three-dimensional treatments (for example, according to a spatial subtraction method, a tomography method, or according to a point cloud reconstruction method) is applied the same way as the method with the previously described four steps.

A first application is the local or regional, dynamic, whether in tendency or in absolute value, dosage of the targeted molecule in the tissue. This dosage aims at determining the concentration, that is to say the ratio between the amount of the targeted molecule on the measurement volume. The three-dimensional maps obtained at the different wavelengths reflecting variable tissue absorption levels are combined and superimposed, so as to be able to derive the dosage therefrom.

For the discrimination of the oxygenated and deoxygenated hemoglobins within the measurement volume, and the dynamic follow-up, in tendency or in absolute value of their proportion within this measurement volume, the optical paths are replicated at at least one other specific wavelength tuned to deoxyhemoglobin (Hb), for example between 650 and 800 nanometers. At least one second three-dimensional map obtained with this different other wavelength will allow, in combination with the first three-dimensional map obtained with the wavelength close to 800 nanometers, representing the levels of oxygenation of the identified various tissue strata. The accuracy of the discrimination of the pursued molecules may be enhanced by increasing the number of wavelengths that are used. The quantification of their absorption related to a target measurement volume (for example volume of the frontal and temporal cortex) enables the local dosage thereof and the calculation of a relative or absolute value of the tissue oxygen saturation (STO2). Besides, still in connection with this known tissue volume, the regional amount of hemoglobin, as well as its concentration, therein may be calculated.

For the dosage of metabolites, other than hemoglobins, the optical paths are replicated at the wavelengths specific to the targeted metabolite, thereby allowing discriminating it, and thus obtaining an in vivo regional dosage of this metabolite, at the level of the organ.

A second application is the determination of the brain vascular volume and of the autoregulation plateau. As hemoglobins circulate in the vascular network, at constant hematocrit, the present disclosure enables a continuous measurement of the variations of absorption at 800 nm, and therefore a measurement of the dynamic variations of the vascular network (vasodilatation and vasoconstriction) under the physiological sensor 1 which conforms to the roundness of the surface of the frontal hemispheres. Thus, with the physiological sensor 1, it is possible to obtain a punctual, and even continuous, and non-invasive measurement of the brain vascular volume after calibration of hematocrit. This physiological datum may be combined with others allowing determining the brain autoregulation threshold of patients.

A third application is the measurement of the vasodilatory reserve and of the endothelial properties.

A fourth application is the assessment of the tissue perfusion in the case of an occlusive peripheral arterial disease of the lower limbs.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, manufacturing technology, and testing capability.

As used herein, the phrase at least one of A, B, and C should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A near-infrared spectroscopy system, comprising a physiological sensor for near-infrared spectroscopy at different depths, said physiological sensor integrating optoelectronic components comprising emitters of near-infrared beams and near-infrared photosensitive receivers, said physiological sensor comprising elementary modules each provided with at least one optoelectronic component, wherein each elementary module is connected to at least one adjacent elementary module by means of one of a plurality of articulations, each articulation configured for a relative movement between the elementary modules of the physiological sensor according to several angles of inclination, wherein the elementary modules of the physiological sensor are assembled at least by means of the articulations connecting the elementary modules and form an optoelectronic spread configurable between:
   a planar configuration according to a main plane in which each articulation has a zero angle of inclination with respect to said main plane, and
   a set of curved conformations in which at least one of the articulations has a non-zero angle of inclination with respect to said main plane; and wherein each articulation between two elementary modules is coupled to an angle sensor configured for a measurement of an angle of inclination defined between the two elementary modules;
   wherein said near-infrared spectroscopy system further comprises a control unit configured to establish spatial coordinates of each emitter and of each receiver according to the angles of inclination of the articulations, wherein said control unit is connected to the emitters of the physiological sensor to activate said emitters in an individual and non-concomitant manner, according to a predefined sequence and to the receivers of the physiological sensor for a recovery and a three-dimensional treatment of measurements originating from the receivers during said predefined sequence according to the spatial coordinates of the emitters and of the receivers, and wherein the control unit is connected to each angle sensor to establish the spatial coordinates of each emitter and of each receiver according to measurement data originating from said angle sensors.

2. The near-infrared spectroscopy system according to claim 1, wherein at least one articulation between two elementary modules is a flexible articulation comprising a flexible strip configured for a relative movement between the two elementary modules by bending of the flexible strip.

3. The near-infrared spectroscopy system according to claim 2, wherein each of the plurality of articulations is a flexible articulation comprising a flexible strip configured for a relative movement between the two elementary modules by bending of the flexible strip.

4. The near-infrared spectroscopy system according to claim 3, wherein each elementary module comprises a rigid or flexible support on which at least one optoelectronic component is disposed, and the flexible strip of the flexible articulation between two elementary modules is connected between the respective supports of said two elementary modules.

5. The near-infrared spectroscopy system according to claim 3, comprising a flexible membrane on which optoelectronic components are disposed and distributed into islets delimiting the elementary modules, wherein the flexible strip of the flexible articulation between two of the elementary modules is formed by a portion of the flexible membrane extending between the islets delimiting said two elementary modules.

6. The near-infrared spectroscopy system according to claim 5, wherein the flexible membrane comprises at least one elastomeric polymer layer in which the optoelectronic components are embedded at least partially.

7. The near-infrared spectroscopy system according to claim 2, wherein, for a flexible articulation comprising the flexible strip, said flexible articulation is coupled to an angle sensor comprising a flexible resistive sensor outputting an angle datum reflecting a variation of resistance as a function of the bending of the flexible strip.

8. The near-infrared spectroscopy system according to claim 7, wherein the flexible resistive sensor is integrated to the flexible strip or is offset with respect to the flexible strip.

9. The near-infrared spectroscopy system according to claim 8, wherein a plurality of the flexible resistive sensors are integrated to a flexible membrane.

10. The near-infrared spectroscopy system according to claim 7, wherein the flexible resistive sensor is integrated to a flexible blade fastened to the flexible strip so that a bending of the flexible strip results in a bending of the flexible blade.

11. The near-infrared spectroscopy system according to claim 10, comprising a flexible film on which a plurality of flexible resistive sensors are disposed, wherein said flexible film is superimposed and fastened on a flexible membrane, and wherein said flexible film defines flexible blades superimposed or offset with respect to flexible strips of the flexible articulations between the elementary modules, said plurality of flexible resistive sensors being provided on said flexible blades.

12. The near-infrared spectroscopy system according to claim 1, wherein at least one articulation between two elementary modules is a semi-rigid articulation configured for a relative movement between the two elementary modules according to several predefined discrete angles of inclination, wherein said semi-rigid articulation is configured to keep a stable inclination between two elementary modules in each of said angles of inclination, and to tilt between two distinct angles of inclination under a force applied on at least one of the two elementary modules.

13. The near-infrared spectroscopy system according to claim 12, wherein a semi-rigid articulation is provided with notches for setting the angle of inclination between the two elementary modules according to several predefined values.

14. The near-infrared spectroscopy system according to claim 13, wherein a semi-rigid articulation is coupled to an angle sensor comprising electrical contactors, wherein each electrical contactor is coupled to a setting notch.

15. The near-infrared spectroscopy system according to claim 12, wherein each semi-rigid articulation is adjustable according to several predefined angles of inclination separated in pairs by a constant angular step.

16. The near-infrared spectroscopy system according to claim 12, wherein each semi-rigid articulation comprises several balls cooperating with an elastic thrust element, said balls being movable within a curved rail with a predefined curvature and sliding inside a guide with a same curvature, and further comprises a cursor on the guide adapted to crush the balls according to the sliding of the rail within the guide, wherein supports linked by the articulation are fastened respectively to one end of the rail and to one end of the guide.

17. The near-infrared spectroscopy system according to claim 1, wherein each one of the elementary modules comprises at least one optoelectronic component selected from the emitters and the receivers and disposed according to at least one of the following arrangements:
- at least one emitter and at least one receiver;
- at least two emitters of signals in distinct lengths in near-infrared;
- at least one emitter disposed at a center of the one of the elementary modules and at least one receiver disposed at a periphery of the one of the elementary modules;
- at least one emitter disposed at the center of the one of the elementary modules and several receivers disposed at the periphery around said emitter;
- at least one emitter and no receiver;
- at least one receiver and no emitter.

18. The near-infrared spectroscopy system according to claim 1, wherein, in the planar configuration of the optoelectronic spread, the elementary modules are distributed into several rows and into several columns orthogonal to the rows.

19. The near-infrared spectroscopy system according to claim 1, wherein each elementary module comprises a rigid or flexible support, on which at least one optoelectronic component is disposed, and each support comprises two opposite and parallel longitudinal edges, and two opposite and parallel transverse edges, and each articulation links two transverse edges contiguous to two adjacent respective supports, namely two longitudinal edges contiguous to two adjacent respective supports.

20. The near-infrared spectroscopy system according to claim 1, wherein, in the planar configuration of the optoelectronic spread, each articulation between two elementary modules is an articulation pivoting about an axis of articulation extending in the main plane.

21. The near-infrared spectroscopy system according to claim 1, wherein the control unit is configured for a three-dimensional treatment of the measurements originating from the receivers during the predefined sequence according to a spatial subtraction method, or according to a tomography method with contrasts maps establishment, or according to a point cloud reconstruction method.

22. The near-infrared spectroscopy system according to claim 21, wherein the control unit is configured for a three-dimensional treatment, at each activation of an emitter, of only measurements originating from receivers selected according to a relative location with respect to said activated emitter established from their spatial coordinates.

23. The near-infrared spectroscopy system according to claim 21, wherein, in the planar configuration of the optoelectronic spread, the elementary modules are distributed into several rows and into several columns orthogonal to the rows, and the control unit is configured to process according to a spatial subtraction method, at each activation of an emitter, the measurements originating from receivers disposed in the same row and in the same column as said emitter.

24. The near-infrared spectroscopy system according to claim 23, wherein the control unit is configured to process according to a spatial subtraction method, at each activation of an emitter, the measurements originating from receivers also disposed in a row and in a column different from those of said emitter.

25. A near-infrared spectroscopy method implementing a spectroscopy system comprising:
- a physiological sensor for near-infrared spectroscopy at different depths, said physiological sensor integrating optoelectronic components comprising emitters of near-infrared beams and near-infrared photosensitive receivers, said physiological sensor comprising elementary modules each provided with at least one optoelectronic component, wherein each elementary module is connected to at least one adjacent elementary module by means of one of a plurality of articulations, each articulation configured for a relative movement between the elementary modules of the physiological sensor according to several angles of inclination, wherein the elementary modules of the physiological sensor are assembled at least by means of the articulations connecting the elementary modules and form an optoelectronic spread configurable between:
- a planar configuration according to a main plane in which each articulation has a zero angle of inclination with respect to said main plane, and
- a set of curved conformations in which at least one of the articulations has a non-zero angle of inclination with respect to said main plane; and wherein each articulation between two elementary modules is coupled to an angle sensor configured for a measurement of an angle of inclination defined between the two elementary modules;
- wherein said near-infrared spectroscopy system further comprises a control unit configured to establish spatial coordinates of each emitter and of each receiver according to the angles of inclination of the articulations, wherein said control unit is connected to the emitters of the physiological sensor to activate said emitters in an individual and non-concomitant manner, according to a predefined sequence and to the receivers of the physiological sensor for a recovery and a three-dimensional treatment of measurements originating from the receivers during said predefined sequence according to the spatial coordinates of the emitters and of the receivers, and wherein the control unit is connected to each angle sensor to establish the spatial coordinates of each emitter and of each receiver according to measurement data originating from said angle sensors;
- said near-infrared spectroscopy method comprising the following steps:
- collection of the measurement data originating from the angle sensors coupled to each articulation;
- establishment of the spatial coordinates of each emitter and of each receiver according to the measurement data originating from the angle sensors;
- activation of the emitters in an individual and non-concomitant manner according to a predefined sequence;
- recovery and three-dimensional treatment of the measurements originating from the receivers during said predefined sequence according to the spatial coordinates of the emitters and of the receivers.

26. The near-infrared spectroscopy method according to claim 25, wherein the three-dimensional treatment of the measurements originating from the receivers during the predefined sequence implements a spatial subtraction method, or a tomography method with contrasts maps establishment, or a point cloud reconstruction method.

27. The near-infrared spectroscopy method according to claim 25, wherein the recovery and treatment step is followed by a step of constructing a three-dimensional image representing a vascular or blood volume within an analysis volume, said vascular or blood volume being composed of voxels constructed from the three-dimensional treatment of the measurements originating from the receivers during the predefined sequence.

28. The near-infrared spectroscopy method according to claim 25, wherein the activation step and the recovery and treatment step are repeated at successive time intervals.

29. The near-infrared spectroscopy method according to claim 25, wherein the spatial coordinates establishment step results in generation of a three-dimensional and virtual optoelectronic imprint of the physiological sensor in place.

30. A physiological sensor for near-infrared spectroscopy at different depths, said physiological sensor integrating optoelectronic components comprising emitters of near-infrared beams and near-infrared photosensitive receivers, said physiological sensor comprising elementary modules each provided with at least one optoelectronic component, wherein each elementary module is connected to at least one adjacent elementary module by means of one of a plurality of articulations, each articulation configured for a relative movement between the elementary modules of the physiological sensor according to several angles of inclination, wherein the elementary modules of the physiological sensor are assembled at least by means of the plurality of articulations and form an optoelectronic spread configurable between:
  a planar configuration according to a main plane in which each of the plurality of articulations has a zero angle of inclination with respect to said main plane, and
  a set of curved conformations in which at least one of the articulations has a non-zero angle of inclination with respect to said main plane; and wherein each articulation between two elementary modules is coupled to an angle sensor configured for a measurement of an angle of inclination between the two elementary modules;
  wherein at least one articulation between two elementary modules is a flexible articulation comprising a flexible strip configured for a relative movement between the two elementary modules by bending of the flexible strip;
  wherein each articulation between two elementary modules is a flexible articulation comprising a flexible strip configured for a relative movement between the two elementary modules by bending of the flexible strip; and
  wherein the physiological sensor comprises a flexible membrane on which optoelectronic components are disposed and distributed into islets delimiting the elementary modules, wherein the flexible strip of the flexible articulation between two elementary modules is formed by a portion of the flexible membrane extending between the islets delimiting said two elementary modules.

31. A physiological sensor for near-infrared spectroscopy at different depths, said physiological sensor integrating optoelectronic components comprising emitters of near-infrared beams and near-infrared photosensitive receivers, said physiological sensor comprising elementary modules each provided with at least one optoelectronic component, wherein each elementary module is connected to at least one adjacent elementary module by means of one of a plurality of articulations configured for a relative movement between the elementary modules of the physiological sensor according to several angles of inclination, wherein the elementary modules of the physiological sensor are assembled at least by means of the plurality of articulations and form an optoelectronic spread configurable between:
  a planar configuration according to a main plane in which each articulation has a zero angle of inclination with respect to said main plane, and
  a set of curved conformations in which at least one of the articulations has a non-zero angle of inclination with respect to said main plane; and wherein each articulation between two elementary modules is coupled to an angle sensor configured for a measurement of an angle of inclination between the two elementary modules;
  wherein at least one articulation between two elementary modules is a flexible articulation comprising a flexible strip configured for a relative movement between the two elementary modules by bending of the flexible strip;
  and wherein, for a flexible articulation comprising the flexible strip, said flexible articulation is coupled to an angle sensor comprising a flexible resistive sensor outputting an angle datum reflecting a variation of resistance as a function of the bending of the flexible strip.

* * * * *